Figure 1:
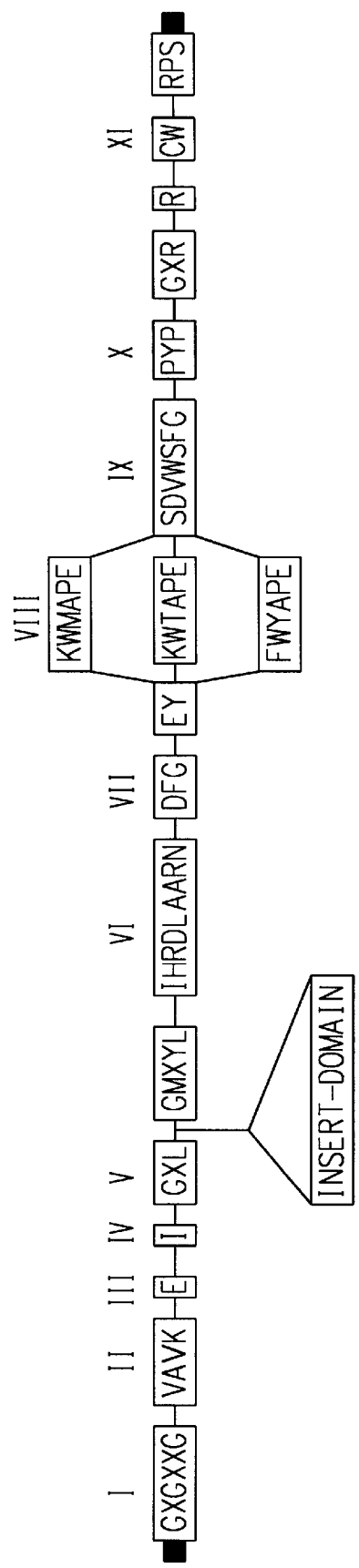

United States Patent [19]

Margolis

[11] Patent Number: 6,037,134
[45] Date of Patent: Mar. 14, 2000

[54] METHODS THAT DETECT COMPOUNDS THAT DISRUPT RECEPTOR TYROSINE KINASE/GRB-7 COMPLEXES

[75] Inventor: Benjamin Lewis Margolis, New York, N.Y.

[73] Assignee: New York University Medical Center, New York, N.Y.

[21] Appl. No.: 08/207,575

[22] Filed: Mar. 7, 1994

[51] Int. Cl.$^7$ .................. G01N 33/574; G01N 33/53; G01N 33/48

[52] U.S. Cl. .................. 435/7.23; 435/7.1; 436/63; 436/64

[58] Field of Search .................. 435/7.23, 7.1; 424/278.1; 436/64, 63

[56] References Cited

U.S. PATENT DOCUMENTS

| | | | |
|---|---|---|---|
| 5,196,446 | 3/1993 | Levitzki et al. | 514/415 |
| 5,217,999 | 6/1993 | Levitzki et al. | 514/613 |

OTHER PUBLICATIONS

Osherov, et al. 1993, Selective Inhibition of the Epidermal Growth Factor and HER2/Neu Receptors by Tryphostins, J. Biol. Chem. 268:11134–42.
Ren et al., 1993, Identification of a Ten–Amino Acid Proline–rich SH3 Binding Site, Science 259:1157–61.
Pawson, T. and Schlessinger, J., 1993, SH2 and SH3 Domains, Current Biol.3(7):434–442.
Mayer and Baltimore, 1993, Trends in Cell. Biol. 3:8–13.
Musacchio et al., 1993, The PH Domain: A Common Piece in the Structural Patchwork of Signalling Proteins, Trends in Biochem. Sci. 18:343–8.
Plowman et al., 1993, Heregulin Induces Tyrosine Phosphorylation of HER4/p180$^{erbB4}$, Nature 366:473–5.
Peles et al., 1993, Cell Type Specific Interaction of Neu Differentiation Factor (HDF/heregulin) with Neu/HER–2 Suggests Complex Ligand–Receptor Relationships, EMBO J. 12:961–71.
Mayer et al., 1993, A Putative Modular Domain Present In Diverse Signalling Proteins, Cell 73:629–30.
Plowman et al., 1993, Lignad–Specific Activation of HER4/p180$^{erbB4}$, a Fourth Member of the Epidermal Growth Factor Receptor Family, PNAS 90:1746–50.
Bowcock et al., 1993, THRA1 and D17S183 Flank an Integral of <4 cM for the Breast–Ovarian Cancer Gene (BRCA1) on Chromosome 17q21, Am. J. Hum. Genetics 52:718–22.
Buday and Downward, 1993, Mol. Cell. Biol. 13:1903–10.
Egan et al., 1993, Association of Sos Ras Exchange Protein with Grb2 is Implicated in Tyrosine Kinase Signal Transduction and Transformation, Nature 363:450–51.
Haslam et al., 1993, Pleckstrin Domain Homology, Nature 363:309–10.
Li et al., 1993, Guanine–Nucleotide–Releasing Factor hSos1 Binds to Grb2 and Links Receptor Tyrosine Kinases to Ras Signalling, Nature 363:85–8.

Skolnick et al., 1993, The SH2/SH3 Domain–Containing Protein GRB2 Interacts with Tyrosine–Phosphorylated IRS1 and SHc: Implications for Insulin Control of ras Signalling, EMBO J. 12:1929–36.
Marini et al., 1993, The Pituitary Hormones Arginine Vasopressin–Neurophysin II and Oxytocin–Neurophysin I Show Close Linkage with Interleukin–1 on Mouse Chromosome 2, Genomics, 15:200–2.
Smith et al., 1993, Topoisomerase IIα co–amplification with erbB2 in Human Primary Breast Cancer and Breast Cancer Cell Lines: Relationship to m–AMSA and mitoxantrone Sensitivity, Oncogene 8:933–8.
Lippman et al., 1993, The Development of Biological Therapies for Breast Cancer, Science 259:631–2.
Schlessinger and Ullrich, 1992, Growth Factor Signalling by Receptor Tyrosine Kinases, Neuron 9:383–91.
Pawson, T. and Gish, J., 1992, SH2 and SH3 Domains: From Structure to Function, Cell 71:359–62.
Scott, JD and Soderling, TR 1992, Serinie/Threonine Protein Kinases, Current Opionion in Neurology 2:289–95.
Ciocca et al., 1992, Correlation of HER–2/neu Amplification with Expression and with Other Prognostic Factors in 1103 Breast Cancers, JNCI 84:1279–82.
Sulston et al., 1992, The *C. elegans* Genome Sequencing Project: A Beginning, Nature 356:37–41.
Posada et al., 1992, Molecular Signal Integration, Interplay Between Serine, Threonine, and Tyrosine Phsophorylation, Mol. Biol. Cell. 3:583–592.
Margolis,B., 1992, Proteins with SH2 Domains: Transducers in the Tryosine Kinase Signalling Pathway, Cell. Growth. Differ. 3:73–80.
Ron and Dressler, 1992, pGSTag–A Versitile Bacterial Expression Plasmid for Enzymatic Labelling of Recombinant Proteins, Blotechniques, 13:866–9.
Rozakis–Adcock et al., 1992, Association of the Shc and Grb2/Sem5 SH2–Containing Proteins Is Implicated in Activation of the Ras Pathway by Tyrosine Kinases, Nature 360:689–92.
Fischer et al., 1991, Protein Tyrosine Phosphatases: A Diverse Family of Intracellular and Transmembrane Enzymes, Science 253:401–6.
Bellacosa et al., 1991, A Retroviral Oncogene, akt Encoding a Serine–Threonine Kinase Containing an SH2–Like Region, Science 254:274–7.

(List continued on next page.)

Primary Examiner—Yvonne Eyler
Attorney, Agent, or Firm—Pennie & Edmonds LLP

[57] ABSTRACT

The present invention relates to compositions and methods for the prevention, prognostic evaluation, and treatment of oncogenic disorders, especially breast cancer, wherein a protein tyrosine kinase capable of complexing with a member of the SH2- and/or SH3-containing family of adaptor proteins is involved. In a preferred embodiment of the invention, the protein tyrosine kinase is the receptor protein tyrosine kinase HER2, and the adaptor protein is GRB, so that the protein tyrosine kinase/adaptor protein complex is a HER2/GRB-7 complex.

10 Claims, 10 Drawing Sheets

OTHER PUBLICATIONS

Pendergast et al., 1991, BCR Sequences Essential for Transformation by the BCR–ABL Oncogene Bind to the ABL SH2 Regulatory Domain in a Non–Phosphotyrosine–Dependent Manner, Cell 66:161–71.

Cantley, et al., 1991, Oncogenes and Signal Transduction, Cell 64:281–302.

Hunter, T., 1991, Cooperation Between Oncogenes, Cell 64:249–70.

Jones et al., 1991, Molecular Cloning and Identification of a Serine/Threonine Protein Kinases of the Second–Messanger Subfamily, PNAS, 88:4171–75.

Hardie, D., 1990, Roles of Protein Kinases and Phosphates in Signal Transduction, Symp. Soc. Exp. Biol. 44:241–255.

Wilks,AF, 1990, Structure and Function of the Protein Tyrosine Kinases, Progress in Growth Fact. Res. 2:97–111.

Kury et al., 1990, Determination of HER–2/neu Amplification and Expression in Tumor Tissue and Cultured Cells Using a Simple, Phenol Free Method for Nucleic Acid Isolation, Oncogene 5:1403–8.

Nurse, P., 1990, Universal Control Mechanism Regulating Onset of M–phase, Nature 344:503–8.

Margolis et al., 1990, Effect of Phospholipase C–γ Overexpression on PDGF–Induced Second Messangers and Mitogenesis, Science 248:607–10.

Sap et al., 1990, Cloning and Expression of a Widely Expressed Receptor Tyrosine Phosphatase, PNAS, 87:6112–6.

Lyall et al., 1989, Tyrophostins Inhibit Epidermal Growth Factor (EGF)–Receptor Tyrosine Kinase Activity in Living Cells and EGF–Stimulated Cell Proliferation, J. Biol. Chem, 264:14503–9.

Buchberg et al., 1989, A Comprehensive Genetic Map of Murine Chromosme 11 Reveals Extensive Linkage Conservation Between Mouse and Human, Genetics 122:153–61.

Lee et al., 1989, HER2 Cytoplasmic Domain Generates Normal Mitogenic and Transforming Signals in a Chimeric Receptor, EMBO J. 8:167–173.

Tavassoli et al., 1989, c–erbB–2/c–erbA Co–amplification Indicative of Lymph Node Metastasis, and c–myc Amplification of High Tumor Grade, in Human Breast Carcinoma, British J. of Cancer 60:505–10.

Slamon et al., 1989, Studies of the HER–2/neu Proto–Oncogene in Human Breast and Ovarian Cancer, Science 244:707–12.

Margolis et al., 1989, EGF Induces Tyrosien Phosphorylation of Phospholipase C–II: A Potential Mechanism for EGF Receptor Signalling, Cell, 57:1101–7.

Gazit et al., 1989, Tyrphostins I: Synthesis and Biological Activity of Protein Tyrosine Kinase Inhibitors, J. Medicinal Chem. 32:2344–52.

Tandon et al., 1989, HER–2/neu Oncogene Protein and Prognosis in Breast Cancer, J. Clin. Oncol. 7:1120–8.

Trahey et al., 1988, Molecular Cloning of Two Types of GAP Complementary DNA from Human Placenta, Science, 242:1697–700.

Stahl et al., 1988, Sequence Similarity of Phospholipase C with the non–catalytic region of src, Nature 332:269–72.

King et al., 1988, EGF Binding to its Receptor Triggers a Rapid Tyrosine Phosphorylation of the erbB–2 Protein in the Mammary Tumor Cell Line SK–BR–3, EMBO J. 7:1647–51.

Mayer et al., 1988, A Novel Viral Oncogene with Structural Similarity to Phospholipase C, Nature 332:272–5.

Tyers et al., 1988, Molecular Cloning and Expression of the Major Protein Kinase C Substrate of Platelets, Nature 333:470–3.

Hanks et al., 1988, The Protein Kinase Family: Conserved Features and Deduced Phylogeny of the Catalytic Domains, Science 241:42–52.

Vogel et al., 1988, Activation of a Phosphotyrosine Phosphatase by Tyrosine Phosphorylation, Science 259:1611–4.

Slamon et al., 1987, Human Breast Cancer: Correlation of Relapse and Survival with Amplification of the HER–2/neu Oncogene, Science 235:177–82.

Van de Vijer et al., 1987, Amplification of the neu (c–erbB–2) Oncogene in Human Mammary Tumors Is Relatively Frequent and Is Often Accompanied by Amplification of the Linked c–erbA Oncogene, Mol. Cel. Biol. 7:2019–23.

Yamamoto et al., 1986, Similarity of Protein Encoded by the Human c–erb–B–2 Gene to Epidermal Growth Factor Receptor, Nature 319:230–234.

Sadowski et al., 1986, A Noncatalytic Domain Conserved Among Cytoplasmic Protein–Tyrosine Kinases Modifies the Kinase Function and Transforming Activity of Fujinami Sarcoma Virus P130$^{gag-fps,}$ Mol. Cell. Biol. 6:4396–408.

Bargman et al., 1986, The neu Oncogene Encodes for an Epidermal Growth Factor Receptor–Related Protein, Nature 319:226–30.

Coussens et al., 1985, Tyrosine Kinase Receptor with Extensive Homology to EGF Receptor Shares Chromosomal Location with neu Oncogene, Science 230:1132–39.

Downward et al., 1984, Close Similarity of Epidermal Growth Factor Receptor and v–erb–B Oncogene Protein Sequences, Nature 307:521–527.

Schechter et al., 1984, The neu Oncogene: an erb–B–related Gene Encoding a 185,000–M Tumor Antigen, Nature 312:513–6.

Padhy et al., 1982, Identification of a Phosphoprotein Specifically Induced by the Transforming DNA of Rat Neuroblatomas, Cell 28:865–71.

Shepard et al, J. Clin. Immunol.,: Monoclonal Antibody therapy of human cancer taking the HER2 Protooncogene to the clinic; vol. 11(3) p. 117–127, 1991.

Margolis et al: High–efficiency expression/cloning of epidermal growth factor–receptor–binding proteins with Src homology 2 domains, PNAS 89:p. 8894–8898, 1992.

Egan et al: Association of SOS RAS exchange protein with Grb2 is implicated in tyrosine kinase signal transduction and transformation, Nature 363:p. 45–51 1993.

Koch et al: SH2 and SH3 Domains: Elements that control Interactions of Cytoplasmic Signaling Proteins, Science 252:p. 668–674, 1991.

Osherov et al: Selective inhibition of the Epidermal Growth Factor and HER2/Neu Receptors by Tyrphostins, J. of Biol. Chem., 268(15):11134–11142, 1993.

Harlow et al,: Antibodies, a laboratory manual, Cold Spring Harbor Laboratory, 1988 p. 424.

```
GRB-7    95   RDssrlc.v  VKvYSEDGac  rsVeVaagaT  arhvcemLvq  RaHalsdEswg
F10E9.6 187   KEakvtkif  VKfFvEDGea  lqLlIderwT  vadtlkqLae  KnHialmEdhc GRB-7   144   LVEshPyLa  LERgLEDHEf  VVEvqeaWpv  ggdsRFiFrK  nfaKYeLfks
F10E9.6 237   IVEeyPeLy  IkRvyEDHEk  VVEniqmWvq  dSpnKLyFmR  rpdKYaFisr GRB-7   193   PphtLFpeKm  vsscldaqtg  isheDLiQnF  L......nag  sfPEiqGFLq
F10E9.6 286   PelyLLtpKt  sdhmeipsgd  qwtiDVkQkF  Vseyfhrepv  vpPEmeGFLy GRB-7   237   LRgsgrgsGR  KlWKRfFcfL  RrSGLYYstK  gtskdpRhLq  yVadVnesnV
F10E9.6 336   LKsd....GR  KsWKKhYfvL  RpSGLYYapK  skkpttKdLt  cLmnLhsnqV GRB-7   287   YvvtqgrKlY  gmPTdFgfcV  KpnkLrnghk  gL.hiFCsED  EqsrtcWLaA
F10E9.6 382   YtgIgweKkY  ksPTpWcisI  KltaLqmkrs  qFikyICaED  EmtfkkWLvA GRB-7   336   FRLfKYGvqL  ykNYqqA..q  sRhlrlsylg  spplrSvsdn  tlVamdFSgH
F10E9.6 432   LRIaKnGaeL  leNYerAcqi  rRetlgpass  msaasSstai  seVphsLShH GRB-7   384   ..........  ..agrvidNP  reaLSaamee  aqawRkktnh  rLSLpttc.S
F10E9.6 482   qrtpsvassi  qlsshmmnNP  thpLSvnv..  ....Rnqspa  sFSVnscqqS GRB-7   421   .gSslSAaI
F10E9.6 526   hpSrtSAkL
```

FIG.8B

|   |   |   |   |   |   |
|---|---|---|---|---|---|
| GRB-7 | 230 | eiqGFLqlRG | sgrgsgrKlW | KrfFcFLrrs | gLYYstKgts |
| F10E9.6 | 329 | emeGFLylKs | d....grKSW | KkHYFVLrps | gLYYApKskk |

| Pleckstrin Consensus (Mayer) | φ+ GFL K G | | W + +φφφ | φφφφ | |
|---|---|---|---|---|---|
| Pleckstrin Consensus (Haslam) | IREGYL KKG<br>VK   W  RR | | KTW K RWFVL<br>RS  R  Y I | D  L L YK<br>G    Y FE | |

|   |   |   |   |   |   |
|---|---|---|---|---|---|
| GRB-7 | 270 | KdPRhLqyVa | dVnesnVyvv | tggrklygmp | tdFgFcVkpn |
| F10E9.6 | 365 | pttKdLtcLm | nLhsnQVytg | igwekkyksp | tpwcIsIklt |

| Pleckstrin Consensus (Mayer) | P Gφφ φ  φ φ | | | NφF  φ  φ | |
|---|---|---|---|---|---|
| Pleckstrin Consensus (Haslam) | PKG   PL | SVCQV<br>VEI | | R    N F  I<br>K    H  L | D |

|   |   |   |   |   |   |
|---|---|---|---|---|---|
| GRB-7 | 310 | klrnghkgl. | hiFcsedeqs | rtcWLaAFrl | F |
| F10E9.6 | 405 | alqmkrsqfi | kyIcAedemt | fkkWLvALri | A |

| Pleckstrin Consensus (Mayer) | | Φ φ φ | -- +--Wφ φφ | φ | |
|---|---|---|---|---|---|
| Pleckstrin Consensus (Haslam) | | FQA S EE<br>LA  T | REEWVKAI<br>KDD M  L | A<br>V | |

FIG. 8C

METHODS THAT DETECT COMPOUNDS THAT DISRUPT RECEPTOR TYROSINE KINASE/GRB-7 COMPLEXES

TABLE OF CONTENTS

1. INTRODUCTION . . .
2. BACKGROUND OF THE INVENTION . . .
   2.1 PROTEIN PHOSPHORYLATION AND SIGNAL TRANSDUCTION . . .
   2.2 PROTEIN TYROSINE KINASES . . .
   2.3 ADAPTOR PROTEINS . . .
   2.4 BREAST CANCER . . .
3. SUMMARY OF THE INVENTION . . .
   3.1. ABBREVIATIONS . . .
4. DESCRIPTION OF THE FIGURES . . .
5. DETAILED DESCRIPTION OF THE INVENTION . . .
   5.1 PROTEIN TYROSINE KINASE/ADAPTOR PROTEIN COMPLEXES . . .
   5.2 TREATMENT OF PTK/ADAPTOR PROTEIN COMPLEX-RELATED ONCOGENIC DISORDERS . . .
      5.2.1 DISRUPTION OF PTK/ADAPTOR PROTEIN COMPLEXES . . .
         5.2.1.1 ANTIBODIES TO PTK/ADAPTOR COMPLEXES . . .
      5.2.2 MODULATION OF ACTIVITY AND/OR LEVEL OF PTK/ADAPTOR COMPLEX COMPONENTS
         5.2.2.1 ANTISENSE AND RIBOZYME APPROACHES . . .
         5.2.2.3 GENE THERAPY . . .
      5.2.3 PHARMACEUTICAL FORMULATIONS, DOSAGES AND MODES OF ADMINISTRATION . . .
   5.3 IDENTIFICATION OF AGENTS FOR TREATMENT OF ONCOGENIC DISORDERS . . .
      5.3.2 PURIFICATION AND PRODUCTION OF PTK/ADAPTOR COMPLEXES . . .
         5.3.2.1 PURIFICATION METHODS . . .
         5.3.2.2 SYNTHESIS AND EXPRESSION METHODS . . .
         5.3.2.3 DERIVATIVES OF PTK/ADAPTOR COMPLEXES . . .
   5.5 PROGNOSTIC EVALUATION OF PTK/ADAPTOR RELATED ONCOGENIC DISORDERS . . .
6. EXAMPLE: GRB-7 LOCALIZES TO MOUSE CHROMOSOME 11 NEAR HER2/ERBB-2 . . .
   6.1 MATERIALS AND METHODS . . .
   6.2 RESULTS . . .
7. EXAMPLE: GRB-7 IS AMPLIFIED AND OVEREXPRESSED IN BREAST CANCER CELL LINES, AND IS OVEREXPRESSED IN BREAST CANCER TISSUE. . .
   7.1 MATERIALS AND METHODS . . .
   7.2 RESULTS . . .
8. EXAMPLE: GRB-7 BINDS TIGHTLY TO HER2 AND ALSO BINDS SHC . . .
   8.1 MATERIALS AND METHODS . . .
   8.2 RESULTS . . .
9. EXAMPLE: GRB-7 IS PHOSPHORYLATED BY THE EGFR/HER2 CHIMERA . . .
   9.1 MATERIALS AND METHODS . . .
   9.2 RESULTS . . .
10. EXAMPLE: PRIMARY SEQUENCE OF GRB-7 REVEALS HOMOLOGY TO A PUTATIVE GENE IN C. ELEGANS AND THE PLECKSTRIN DOMAIN . . .
    10.1 MATERIALS AND METHODS . . .
    10.2 RESULTS . . .
11. EXAMPLE: SCREENING ASSAY FOR INHIBITORS OF ADAPTOR PROTEIN TYROSINE KINASE INTERACTION . . .

1. INTRODUCTION

The present invention relates to compositions and methods for the prevention, prognostic evaluation, and treatment of oncogenic disorders, especially breast cancer, wherein a protein tyrosine kinase capable of complexing with a member of the SH2-and/or SH3-domain containing family of adaptor proteins is involved.

Specifically, the present invention relates to compositions and methods for decreasing or inhibiting the interaction between the components of protein tyrosine kinase/adaptor protein complexes, and/or decreasing or inhibiting the activity of such complexes, especially HER2/GRB-7 complexes, and to methods for the identifying such agents. Further, the present invention relates to the use of such methods and compositions for the treatment of the oncogenic disorders of interest, especially breast cancer. Still further, the present invention relates to compositions and methods for the treatment of oncogenic disorders, especially breast cancer, which involve modulating the activity and/or level of individual components of the protein tyrosine kinase/adaptor protein complexes, and additionally relates to methods for the identification of agents for such treatments.

2. BACKGROUND OF THE INVENTION

2.1 PROTEIN PHOSPHORYLATION AND SIGNAL TRANSDUCTION

Cells rely, to a great extent, on extracellular molecules as a means by which to receive stimuli from their immediate environment. These extracellular signals are essential for the correct regulation of such diverse cellular processes as differentiation, contractility, secretion, cell division, contact inhibition, and metabolism. The extracellular molecules, which can include, for example, hormones, growth factors, lymphokines, or neurotransmitters, act as ligands that bind specific cell surface receptors. The binding of these ligands to their receptors triggers a cascade of reactions that brings about both the amplification of the original stimulus and the coordinate regulation of the separate cellular processes mentioned above. In addition to normal cellular processes, receptors and their extracellular ligands may be involved in abnormal or potentially deleterious processes such as virus-receptor interaction, inflammation, and cellular transformation to a cancerous state.

A central feature of this process, referred to as signal transduction (for reviews, see Posada, J. and Cooper, J. A., 1992, Mol. Biol. Cell 3:583–592; Hardie, D. G., 1990, Symp. Soc. Exp. Biol. 44:241–255), is the reversible phosphorylation of certain proteins. The phosphorylation or dephosphorylation of amino acid residues triggers changes, such as in conformation, in regulated proteins that alter their biological properties. Proteins are phosphorylated by protein kinases and are dephosphorylated by protein phosphatases. Protein kinases and phosphatases are classified according to the amino acid residues they act on, with one class being serine-threonine kinases and phosphatases (reviewed in Scott, J. D. and Soderling, T. R., 1992, Current Opinion in Neurobiology 2:289–295), which act on serine and threonine residues, and the other class being the tyrosine kinases and phosphatases (reviewed in Fischer, E. H. et al., 1991, Science 253:401–406; Schlessinger, J. and Ullrich, A., 1992, Neuron 9:383–391; Ullrich, A. and Schlessinger, J., 1990, Cell 61:203–212), which act on tyrosine residues. The protein kinases and phosphatases may be further defined as being receptors, i.e., the enzymes are an integral part of a transmembrane, ligand-binding molecule, or as non-receptors, meaning they respond to an extracellular molecule indirectly by being acted upon by a ligand-bound receptor. Phosphorylation is a dynamic process involving competing phosphorylation and dephosphorylation reactions, and the level of phosphorylation at any given instant reflects the relative activities, at that instant, of the protein kinases and phosphatases that catalyze these reactions.

While the majority of protein phosphorylation occurs at serine and threonine amino acid residues, phosphorylation at tyrosine residues also occurs, and has begun to attract a great deal of interest since the discovery that many oncogene products and growth factor receptors possess intrinsic protein tyrosine kinase activity. The importance of protein tyrosine phosphorylation in growth factor signal transduction, cell cycle progression, metastasis, and neoplastic transformation is now well established (Cantley, L. C. et al., 1991, Cell 64:281–302; Hunter T., 1991, Cell 64:249–270; Nurse, 1990, Nature 344:503–508; Schlessinger, J. and Ullrich, A., 1992, Neuron 9:383–391; Ullrich, A. and Schlessinger, J., 1990, Cell 61:203–212). Subversion of normal growth control pathways leading to oncogenesis has been shown to be caused by activation or overexpression of protein tyrosine kinases which constitute a large group of dominant oncogenic proteins (reviewed in Hunter, T., 1991, Cell 64:249–270).

2.2 PROTEIN TYROSINE KINASES

Protein tyrosine kinases comprise a large family of proteins, including many growth factor receptors and potential oncogenes, which share ancestry with, but nonetheless differ from, serine/threonine-specific protein kinases (Hanks et al., 1988, Science 241:42–52).

Receptor-type protein tyrosine kinases having a transmembrane topology have been studied extensively. The binding of a specific ligand to the extracellular domain of a receptor protein tyrosine kinase is thought to induce receptor dimerization and phosphorylation of their own tyrosine residues. Individual phosphotyrosine residues of the cytoplasmic domains of receptors may serve as specific binding sites that interact with a host of cytoplasmic signalling molecules, thereby activating various signal transduction pathways (Ullrich, A. and Schlessinger, J., 1990, Cell 61:203–212).

The intracellular, cytoplasmic, non-receptor protein tyrosine kinases, may be broadly defined as those protein tyrosine kinases which do not contain a hydrophobic, transmembrance domain. Members of the various morphotypic families of cytoplasmic protein tyrosine kinases which have been identified share non-catalytic domains in addition to sharing their catalytic kinase domains. Such non-catalytic domains include the SH2 (SRC homology domain 2; Sadowski, I. et al., Mol. Cell. Biol. 6: 4396–4408; Koch, C. A. et al., 1991, Science 252:668–674) domains and SH3 domains (SRC homology domain 3; Mayer, B. J. et al., 1988, Nature 332:269–272). The non-catalytic domains are thought to be important in the regulation of protein-protein interactions during signal transduction (Pawson, T. and Gish, G., 1992, Cell 71:359–362).

2.3 ADAPTOR PROTEINS

Intracellular proteins having characteristic conserved peptide domains (SH2 and/or SH3 domains, as described below) which are critical to the signal transduction pathway. Such proteins, which may be termed adaptor proteins, link protein tyrosine kinases, especially receptor-type protein tyrosine kinases to downstream intracellular signalling pathways such as the RAS signalling pathway. It is thought that such adaptor proteins may be involved in targeting signal transduction proteins to the correct site in the plasma membrane or subcellular compartments, and may also be involved in the regulation of protein movement within the cell.

Such adaptor proteins are among the protein substrates of the receptor-type protein tyrosine kinases, and have in common one or two copies of an approximately 100 amino acid long motif. Because this motif was originally identified in c-Src-like cytoplasmic, non-receptor tyrosine kinases it is referred to as a Src homology 2 (SH2) domain. SH2-containing polypeptides may otherwise, however, be structurally and functionally distinct from one another (Koch, C. A. et al., 1991, Science 252:668–674). SH2 domains directly recognize phosphorylated tyrosine amino acid residues. The peptide domains also have independent sites for the recognition of amino acid residues surrounding the phosphotyrosine residue(s).

When a receptor protein tyrosine kinase binds an extracellular ligand, receptor dimerization is induced, which, in turn, leads to intermolecular autophosphorylation of the dimerized kinases (Schlessinger, J. and Ullrich, A., 1992, Neuron 9: 383–391). Receptor phosphorylation, therefore, creates SH2-binding sites, to which an adaptor protein may bind.

In addition to SH2 peptide domains, many of the adaptor proteins involved in signal transduction contain a second conserved motif of 50–75 amino acids residues, the SH3 domain (Schlessinger, J. and Ullrich, A., 1992, Neuron 9:383–391; Pawson, T. and Gish, G. D., 1992, Cell 72:359–362; Mayer, B. J. and Baltimore, D., 1993, Trends in Cell Biol. 3 8–13; Mayer, B. J. et al., 1988, Nature 352:272–275). Much less is known about the biological role of the SH3 domain than is known about the role of SH2. The current view is that SH3 domains function, in part, as protein-binding domains that act to link signals transmitted from the cell surface to downstream effector genes such as ras (Pawson, T. and Schlessinger, J., 1993 Current Biology, 3:434–442).

2.4 BREAST CANCER

Growth factors and their receptors are crucial for normal development but can also act as oncogenes leading to cell transformation and cancer. Among women, breast cancer is by far the leading cause of cancer, with invasive breast cancer affecting approximately one woman in nine. (Lippman, M. E., 1993, Science 259:631–632).

A number of proteins have been identified which may participate in the aberrant growth of breast cancer cells. Such proteins include p53, a transcriptional regulator with tumor suppressor properties, nm23, a putative metastasis suppressor, and several families of cell surface growth factor receptors and their cognate ligands, including the epidermal growth factor (EGF) receptor superfamily, the insulin-like growth factor (IGF-1) family, and the fibroblast growth factor (FGF) family. For example, HER2, a receptor with close similarity to EGF-Receptor, also known as c-erBb-2 (Coussens et al., 1985, Science 230:1132–1139; Yamamoto et al., 1986, Nature 319:230–234; King et al., 1985, Nature 307:521–527) has been identified. This receptor was also isolated as the rat oncogene neu, an oncogene responsible for chemically induced rat glioblastomas (Padhy et al., 1982, Cell 28:865–871; Schechter et al., 1984, Nature 312:513–516; Bargmann et al., 1986, Nature 319:226–230).

HER2/erbB-2 is known to be amplified and overexpressed in about 25% of human breast cancers (Slamon et al., 1987, Science 235:177–182; Slamon et al., 1989, Science 244:707–712).

To date, however, none of the identified proteins has yielded a successful clinical therapy. That is, while great progress has been made in detection and treatment of localized disease, there has been only relatively modest progress in the treatment of advanced disease. Clearly, new therapeutic approaches are needed.

3. SUMMARY OF THE INVENTION

The present invention relates to compositions and methods for the prevention, prognostic evaluation, and treatment of oncogenic disorders, especially breast cancer, wherein a protein tyrosine kinase capable of complexing with a member of the SH2- and/or SH3-containing family of adaptor proteins is involved.

Specifically, the present invention relates to compositions and methods for decreasing or inhibiting the interaction between the components of protein tyrosine kinase/adaptor protein complexes, and/or decreasing or inhibiting the activity of such complexes, especially HER2/GRB-7 complexes, and to methods for identifying such agents. Further, the present invention relates to the use of such methods and compositions for the treatment of the oncogenic disorders of interest, especially breast cancer. Still further, the present invention relates to compositions and methods for the treatment of oncogenic disorders, especially breast cancer, which involve modulating the activity and/or level of individual components of the protein tyrosine kinase/adaptor protein complexes, and relates to methods for the identification of agents for such treatments. Additionally, the present invention relates to methods and compositions for prognostic evaluation of oncogenic disorders, especially breast cancer, which involve protein tyrosine kinase capable of complexing with a member of the SH2- and/or SH3-containing family of adaptor proteins.

"Protein tyrosine kinase" will, herein, be abbreviated "PTK". It is to be understood that "PTK" may refer to either a transmembrane, receptor-type protein tyrosine kinase or a cytoplasmic protein tyrosine kinase, unless otherwise indicated.

This invention is based, in part, on the discovery that an adaptor protein, GRB-7, is overexpressed in several different breast cancer cell lines and in tissue samples from primary human breast cancer, and, further, on the discovery that GRB-7 is amplified in concert with the receptor tyrosine kinase molecule HER2, a signal transduction molecule implicated in the development of breast cancer. The present invention is further based on the surprising discovery that GRB-7, via its SH2 domain, tightly binds HER2, and that, in fact, a large fraction of tyrosine phosphorylated HER2 in the breast cancer cell line SKBR-3 is bound to GRB-7. The data representing these discoveries is presented in the Working Examples in Sections 7 and below. Additional Working Examples demonstrate that GRB-7 maps to human chromosome region 17q near HER2 and the breast cancer susceptibility gene, BRCA1 (Section 6), GRB-7 forms a complex with the tyrosine phosphorylated protein SHC (Section 8), GRB-7 is phosphorylated by activated HER2 (Section 9), and it is shown that GRB-7 contains a pleckstrin domain, a domain that functions in binding to other regulatory factors (Section 10). The Example presented in Section 11 involves a screening assay for the identification of substances that inhibit the physical interaction between an adaptor protein (GRB-7 in this Example) and an activated tyrosine kinase molecule (HER2, in this Example).

3.1. ABBREVIATIONS

| Amino Acid | One Letter code | Three Letter Code |
|---|---|---|
| Alanine | A | Ala |
| Arginine | R | Arg |
| Asparagine | N | Asn |
| Aspartic Acid | D | Asp |
| Cysteine | C | Cys |
| Glutamic Acid | E | Glu |
| Glutamine | Q | Gln |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| Not specified | X | |

4. DESCRIPTION OF THE FIGURES

FIG. 1. Conserved motifs of the catalytic domains of PTKS (SEQ ID NOS:1–8). (From Wilks, A. F., 1990, Progress in Growth Fact. Res. 2:97–111).

Figures 2A, 2B:
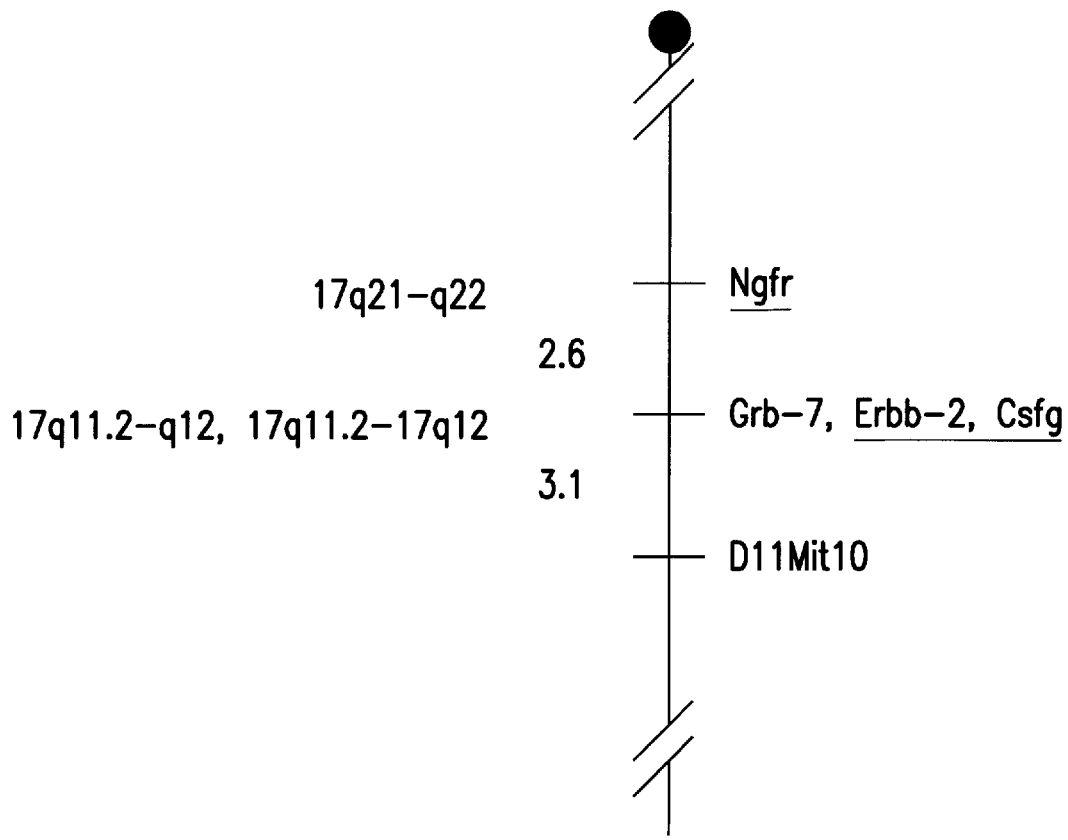

FIG. 2A. Summary of the results of the interspecific backcross analysis demonstrating that GRB-7 maps on chromosome II near to erbB2/HER2. Genes mapped in the analysis are listed on the left. Each column represents the chromosome identified in the N2 progeny inherited from the (AEJ/GN×M. spretus) F1 parent. The closed boxes represent the AEJ/GN allele and the open boxes represent the M. spretus allele. The number of each type of chromosome identified in the backcross progeny are listed at the bottom.

FIG. 2B. Genetic localization of GRB-7. The figure represents the region of mouse chromosome 11 analyzed in the interspecific backcross. The genes mapped are listed on the right and the genetic map distance (in cMs) between adjacent loci, are listed on the left of the chromosome. The location of the human homologues of the genes are listed on the extreme left.

Figure 3A:
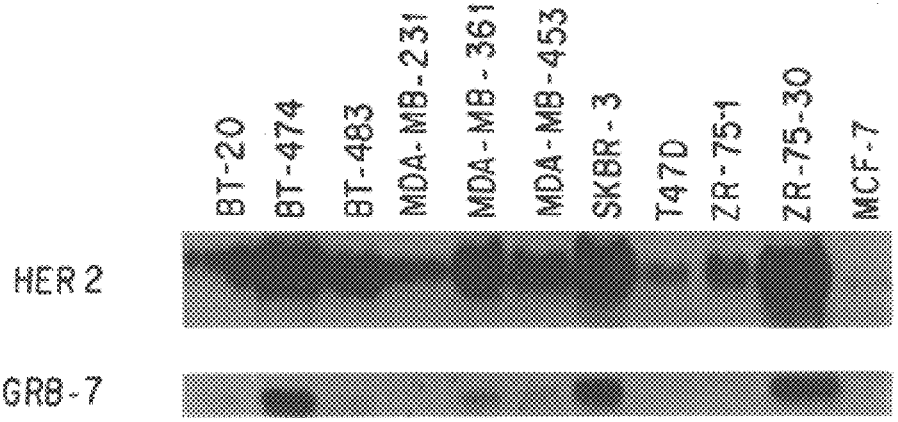

FIG. 3A. Immunoblotting of GRB-7 in breast cancer cell lines. Two hundred micrograms of protein from cell lysates were run on an sodium dodecyl sulfate-polyacrylamide gel electrophoresis (SDS-PAGE) gel and transferred to nitrocellulose. The nitrocellulose was then blocked and probed with either anti-GRB-7 (#188) antibody or anti-HER2 antibody. After detection with $^{125}$I-protein A, blots were exposed to film. The HER2 blot, top, was exposed for 4 hours and the GRB-7 blot, bottom, was exposed for 12 hours.

Figure 3B:
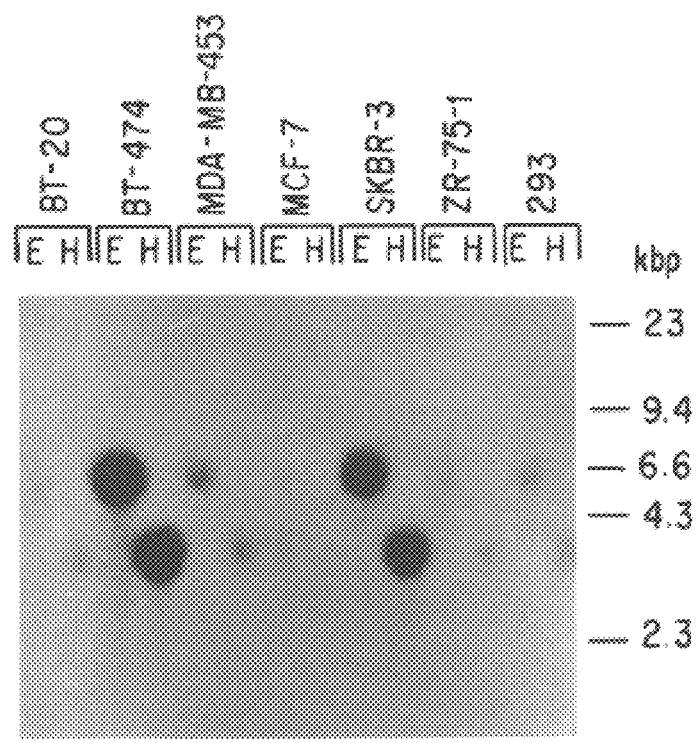

FIG. 3B. Southern blotting of GRB-7 in breast cancer cell lines. Ten micrograms of genomic DNA was digested with either EcoR1 (E) or Hind III (H) and separated on a 0.7% agarose gel. All lanes represent breast cancer cell lines except 293 cells (human embryonic kidney), which were used as a control. Blotting and hybridization was carried out with a GRB-7 probe as described in the Section 6.1, below.

Figure 3C:

FIG. 3C. Immunoblotting of GRB-7 in breast tumors. Frozen pulverized tumor powder was lysed in 5% SDS as described (Tandon et al., 1989, J. Clin. Oncol. 7:1120–1128)

and 100 μg of total solubilized protein was run on an SDS-PAGE gel, transferred to nitrocellulose, and immunoblotted with anti-GRB-7 (#188) antibody. After detection with $^{125}$I-anti-rabbit sera (Amersham), the nitrocellulose blots were exposed to film. A representative blot of ten tumors is shown. All tumors overexpressed HER2 except #5. With the exception of #3 and #5, all tumors were considered positive for GRB-7 expression.

Figure 4A:
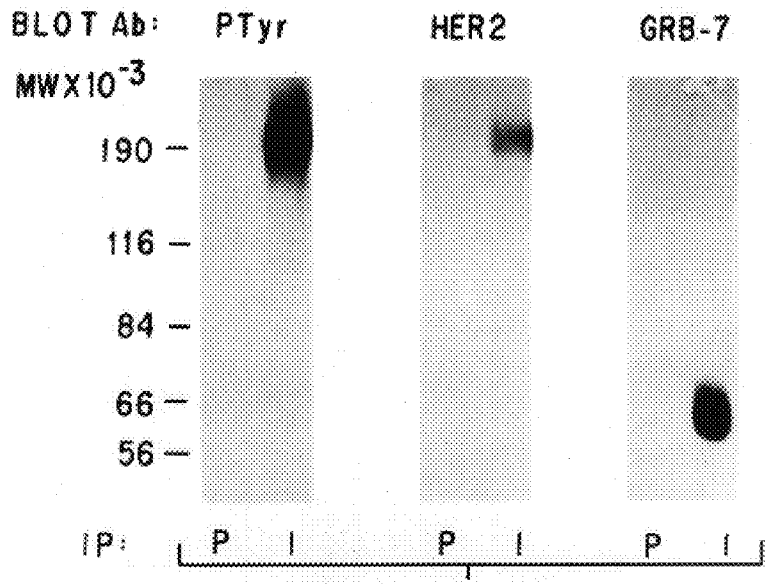

FIG. 4A. Coimmunoprecipitation of HER2 and GRB-7. SKBR-3 cells were starved overnight in serum free medium and then lysed in 1% Triton X-100 lysis buffer with phosphatase and protease inhibitors. Lysates were then immunoprecipitated with anti-GRB-7 (I) antibodies or preimmune (P) serum and separated by SDS-PAGE. After transfer to nitrocellulose, blots were probed with phosphotyrosine (PTyr), HER2 or GRB-7 (#188) antibodies. Blots were detected as in FIG. 3A. HER2 and PTyr blots represent immunoprecipitations from 2.5 μg of cellular protein, while the GRB-7 blot is an immunoprecipitation from 1 μg of protein. GRB-7 and PTyr blots were exposed for 14 hours while the HER2 blot was exposed for 4 hours.

Figure 4B:
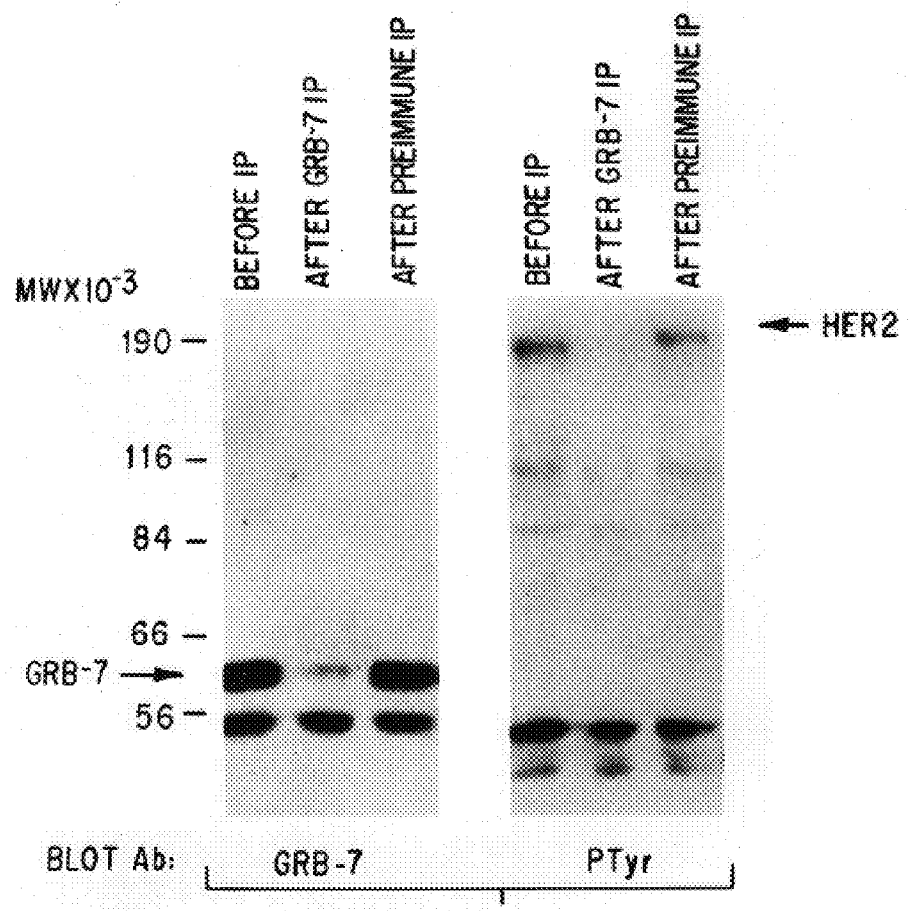

FIG. 4B. GRB-7 immunoprecipitation clears tyrosine phosphorylated HER2 from SKBR-3 cell lysates. Five hundred micrograms of cell lysate from starved SKBR-3 cells was immunoprecipitated with 20 μl of preimmune or anti-GRB-7 (#222) serum. Lysates (130 μg) from before and after the immunoprecipitations were then immunoblotted with anti-Ptyr and antiGRB-7 (#188) to determine what fraction of GRB-7 and tyrosine phosphorylated HER2 was cleared from the lysate by immunoprecipitation. The band at 56 kDa in the GRB-7 blot is an unidentified protein recognized by affinity purified antibody #188. It is not recognized by any of the other GRB-7 antibodies in immunoprecipitation or immunoblotting. Exposure time was 14 hours.

Figure 5A:
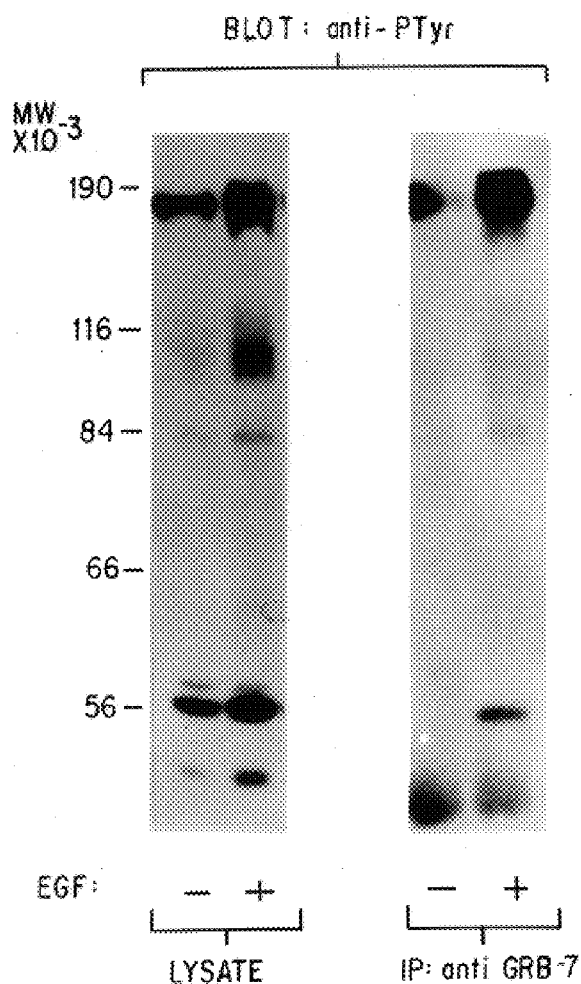

FIG. 5A. GRB-7 antisera coimmunoprecipitates SHC from EGF stimulated SKBR-3 cell lysates. SKBR-3 cells were starved in serum free media overnight and then treated with (+) or without (-) 200 nM EGF for 3 minutes. After cell lysis, immunoprecipitation was performed with affinity purified anti-GRB-7 (#222). Immunoprecipitates and cell lysate (130 μg) were then run on SDS-PAGE and transferred to nitrocellulose and immunoblotted with antiphosphotyrosine (PTyr).

Figure 5B:
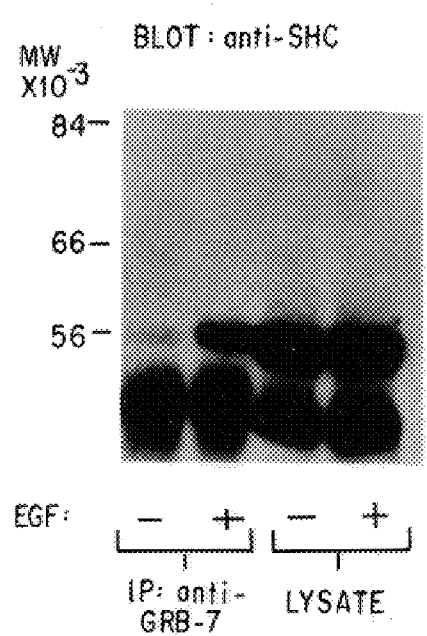

FIG. 5B. GRB-7 antisera coimmunoprecipitates SHC from EGF stimulated SKBR-3 cell lysates. SKBR-3 cells were starved in serum free media overnight and then treated with (+) or without (-) 200 nM EGF for 3 minutes. After cell lysis, immunoprecipitation was performed with affinity purified anti-GRB-7 (#222). Immunoprecipitates and cell lysate (130 μg) were then run on SDS-PAGE and transferred to nitrocellulose and immunoblotted with anti-SHC antibodies. In the immunoblot, the band at approximately 50 kDa represents the IgG heavy chain in the GRB-7 immunoprecipitate, while in the cell lysate it represents the 46 kDa form of SHC.

Figure 6A:
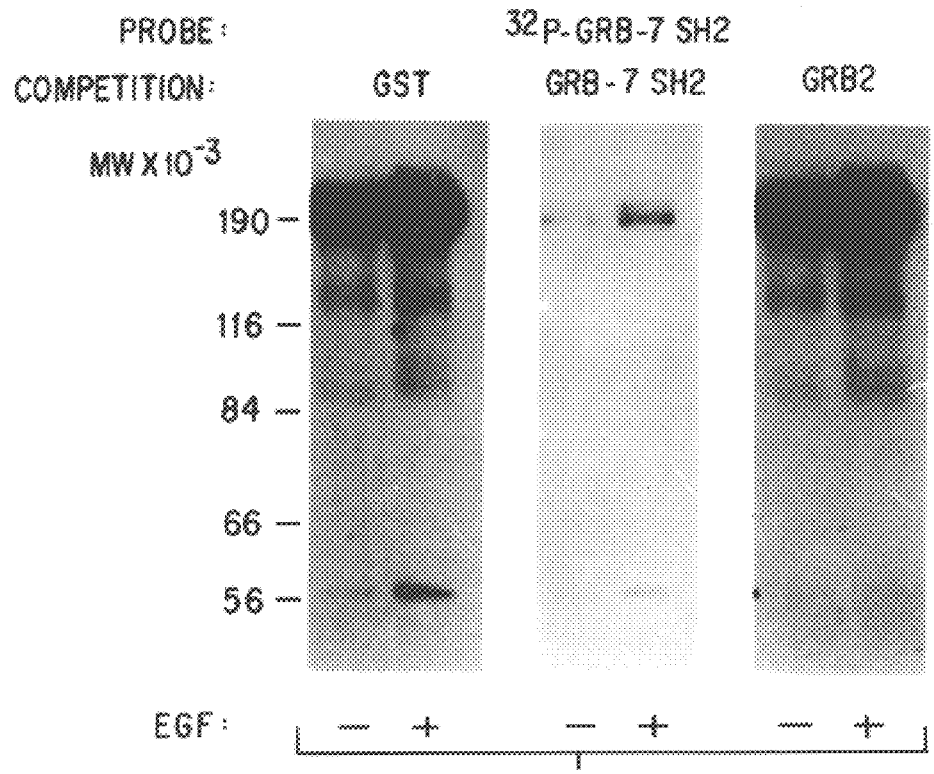

FIG. 6A. Binding of GRB-7 SH2 domain to SKBR-3 lysates. GST fusion protein of GRB-7 SH2 domain was prepared in a GST vector that incorporates a protein kinase A phosphorylation site. The fusion protein was labelled using protein kinase A and $\gamma^{32}$p-ATP as described in Section 10.1, below. SKBR-3 lysates, treated with or without EGF, were separated by SDS-PAGE and transferred to nitrocellulose. These blots were blocked for 2 hours at room temperature in 5% nonfat milk and incubated with 12.5 ng/ml (specific activity $2 \times 10^7$ cpm/μg) of probe. Included with the probe was a 100 fold molar excess of either GST, GRB-7 SH2 or GRB2 protein. After two hours of incubation, the blots were washed four times with Tris buffered saline containing 0.1% Triton X100 and exposed to X-ray film. Exposure time was 12 hours.

Figure 6B:
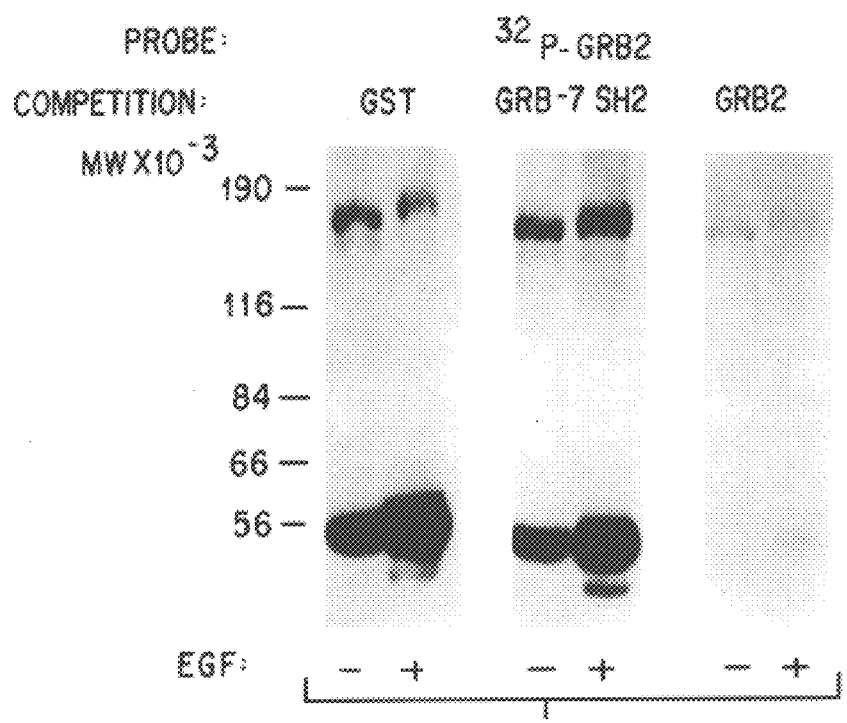

FIG. 6B. Binding of GRB-2 to SKBR-3 lysates. GST fusion protein of full length GRB2 was prepared in a GST vector that incorporates a protein kinase A phosphorylation site. The fusion protein was labelled using protein kinase A and $\gamma^{32}$p-ATP as described in Section 10.1, below. SKBR-3 lysates, treated with or without EGF were then separated by SDS-PAGE and transferred to nitrocellulose. These blots were blocked for 2 hours at room temperature in 5% nonfat milk and incubated with 12.5 ng/ml (specific activity $2 \times 10^7$ cpm/μg) of probe. Included with the probe was a 100 fold molar excess of either GST, GRB-7 SH2 or GRB2 protein. After two hours of incubation, the blots were washed four times with Tris buffered saline containing 0.1% Triton X100 and exposed. Exposure time was 2 hours.

Figure 7A:
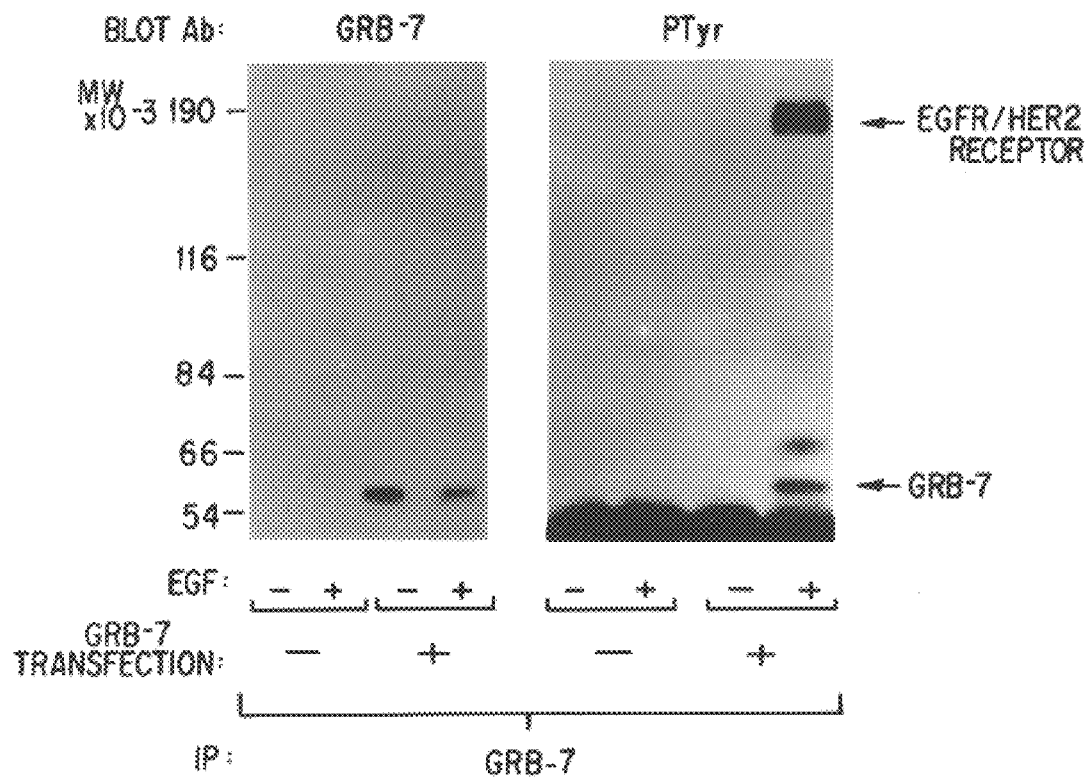

FIG. 7A. Tyrosine phosphorylation of GRB7. Cells expressing the EGFR/HER2 chimera with and without GRB-7 were starved in serum free media for 48 hours and then treated with EGF for 3 minutes. Lysates (1.5 mg protein) were immunoprecipitated with GRB-7 antibodies and separated by SDS-PAGE. After transfer to nitrocellulose, blots were probed with anti-PTyr (right) or anti-GRB-7 (left) antibodies. Eighty percent of the immunoprecipitate was run for anti-PTyr blot and twenty percent for GRB-7 blot.

Figure 7B:
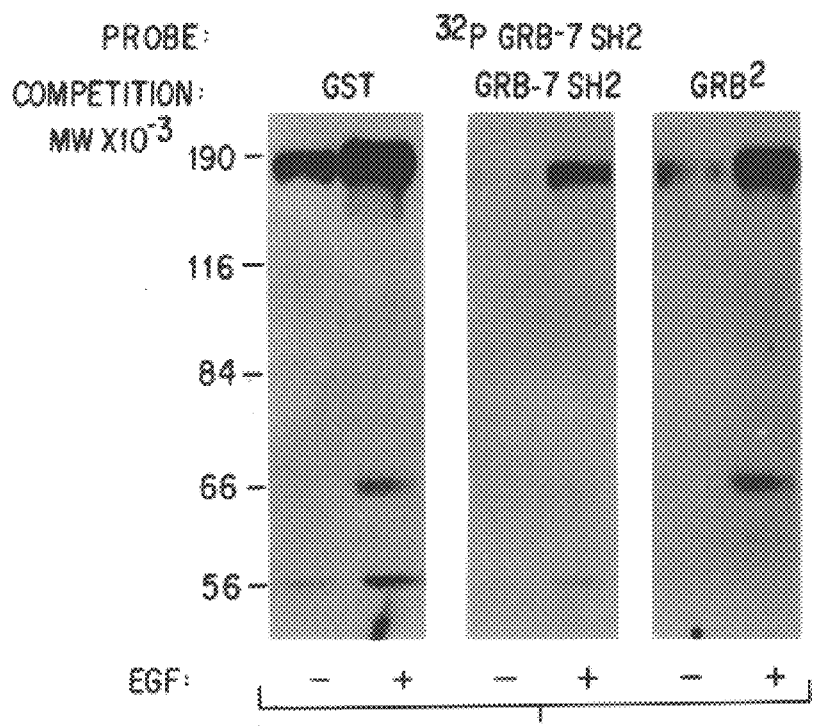

FIG. 7B. GRB-7 SH2 domain associates with three proteins in NIH 3T3 cells expressing the EGFR/HER2 chimera. Cells were treated as in FIG. 7A, lysates (50 μg) from cells expressing the chimeric receptor were run out on SDS-PAGE and transferred to nitrocellulose. Blots were then probed as in FIGS. 6A and 6B with $^{32}$P-GRB-7 SH2 domain.

Figure 8A:
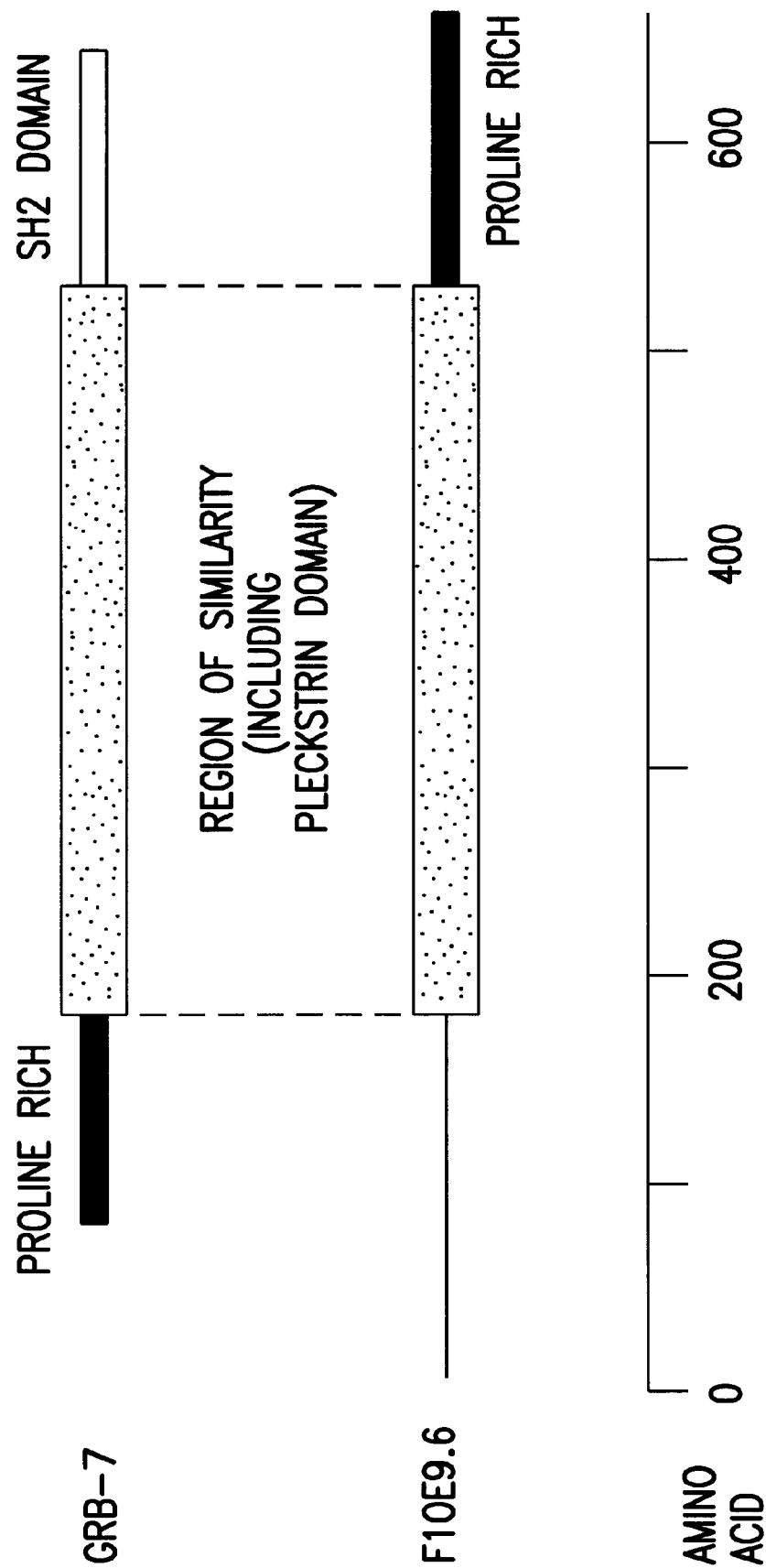

FIG. 8A. Schematic representation of GRB-7 and F10E9.6. F10E9.6 represents a putative gene derived from genomic sequence of C. elegans using the program Genefinder (Sulston et al., 1992, Nature 356:37–41). The sequences were deposited by the C. elegans Sequencing Consortium, Genbank accession number L10986 (Sulston et al., 1992, Nature, 356:37–41). The region of GRB-7/F10E9.6 similarity, including the pleckstrin domain, the genes' respective proline-rich regions, and the GRB-7 SH2 domain are schematically represented.

FIG. 8B. Alignment of the region of similarity between GRB-7 (SEQ ID NO:9) and F10E9.6(SEQ ID NO:10). Alignment was performed using the GCG Bestfit program. Bold capital letters indicate identity and plain capital letters indicate conservative substitution, as defined by a score greater than 0.8 on the PAM 250 scoring table (Schwartz and Dayhoff, eds., 1979, Atlas of Protein Sequences and Structure, pp. 353–358, National Biomedical Research Foundation, Washington, D.C.)

FIG. 8C. Alignment of GRB-7 and F10E9.6 with the consensus sequences for pleckstrin domain. Bold capital letters indicate agreement with the consensus sequence as defined by both Mayer SEQ ID NO:11 (Mayer et al., 1993, Cell, 73:629–630) and Haslam SEQ ID NO:12 (Haslam et al., 1993, Nature, 363:309–310) while plain capital letters indicate agreement with only one of the consensus sequences. φ represents a hydrophobic residue, and Φ represents an aromatic residue.

5. DETAILED DESCRIPTION OF THE INVENTION

Described herein are compositions and methods for the prevention, prognostic evaluation, and treatment of oncogenic disorders, especially breast cancer, in which a protein tyrosine kinase capable of complexing with a member of the SH2-and/or SH3-containing family of adaptor proteins is involved.

First, methods and compositions for the treatment of oncogenic disorders, especially breast cancer, are described. Such methods and compositions may include, but are not limited to the agents capable of decreasing or inhibiting the interaction between the components of protein tyrosine kinase/adaptor protein complexes, agents capable of inhibiting or decreasing the activity of such complexes, agents capable of modulating the activity and/or level of individual components of the protein tyrosine kinase/adaptor protein complexes, and the use and administration of such agents.

Second, methods are described for the identification of such agents. These methods may include, for example, assays to identify agents capable of disrupting or inhibiting the interaction between components of the protein tyrosine kinase/adaptor protein complexes, and may also include paradigms and strategies for the rational design of drugs capable of disruption and/or inhibition of such complexes.

Additionally, methods and compositions are discussed for the prognostic evaluation of oncogenic disorders, especially breast cancer, which involve a protein tyrosine kinase capable of complexing with a member of the SH2- and/or SH3-containing family of adaptor proteins.

This invention is based, in part, on the discovery that the adaptor protein GRB-7 is overexpressed in several different breast cancer cell lines and in tissue samples from primary human breast cancer. The present invention is based, additionally, on the discovery that GRB-7 is amplified in concert with the receptor tyrosine kinase molecule HER2, a signal transduction molecule implicated in the development of breast cancer. Further, this invention is based, in part, on the surprising discovery that GRB-7 tightly binds HER2, and that, in fact, a large fraction of tyrosine phosphorylated HER2 in the breast cancer line SKBR-3 is bound to GRB-7. The Working Examples presented, below, in Sections 7 and 8, represent the data underlying these discoveries. Additionally, Working Examples presented below, demonstrate that GRB-7 maps to a region on human chromosome region 17q, near HER2 and the breast cancer susceptibility gene BCRA1 (Section 6), GRB-7 forms a complex with the tyrosine phosphorylated protein SHC (Section 8), GRB-7 is phosphorylated by activated HER2 (Section 9), and it is shown that GRB-7 contains a pleckstrin domain, a domain that may function in binding to other regulatory factors (Section 10). The Example presented in Section 11 involves a screening assay for the identification of substances that inhibit the physical interaction between an adaptor protein (GRB-7 in this Example) and an activated tyrosine kinase molecule (HER2, in this Example).

Where necessary for clarity of discussion, the invention is described in the subsections below by way of example for the receptor protein tyrosine kinase HER2, the adaptor protein GRB-7, and the resulting HER2/GRB-7 complex. The principles discussed herein, however, may be applied to other members of the protein tyrosine kinase class of molecules and to other members of the SH2 and/or SH3 domain-exhibiting class of adaptor proteins, and to complexes formed by such protein tyrosine kinase molecules and adaptor molecules.

5.1 PROTEIN TYROSINE KINASE/ADAPTOR PROTEIN COMPLEXES

The PTK/adaptor protein complexes of the invention comprise at least one member of the PTK family of proteins, and/or a derivative thereof, and at least one member of the adaptor family of proteins, or a derivative thereof, as described below. Under standard physiological conditions, the components of such complexes are capable of forming stable, non-covalent attachments with one or more of the other PTK/adaptor protein complex components. Methods for the purification and production of such PTK/adaptor protein complexes and of cells that exhibit such complexes are described, below, in Section 5.3.2.

The PTK components of the PTK/adaptor protein complexes of the invention are either cytoplasmic, intracellular, non-receptor PTKs or transmembrane, receptor-type PTKs or derivatives thereof, each of which comprises one or more characteristic peptide domains. Such domains may include one or more catalytic domains which may include, but are not limited to, a tyrosine kinase domain. A tyrosine kinase catalytic domain generally ranges in length from about 250 to about 300 amino acids, corresponding to a molecular weight of approximately 30 kDa. The location of the tyrosine kinase catalytic domain, while not fixed, is generally near the carboxyl terminus of its protein. Short, conserved, stretches of amino acid residues may be present within the tyrosine kinase domain, which alternate in sequence with variable-length stretches of amino acid residues which do not exhibit a high level of conservation. The consensus sequences, corresponding to the most highly conserved of the tyrosine kinase catalytic domain amino acid residues have been compiled and are well known to those of ordinary skill in the art. See, for example, Hanks et al. (Hanks, S. K. et al., 1991, Science 241:42–52), and Wilks (Wilks, A. F., 1990, Prog. Growth Factor Res. 2:97–111) which are incorporated herein, by reference, in their entirety. Among such consensus sequences are the PTK-specific sequences D-L-R-A-A-N (SEQ ID NO:18) or D-L-A-A-R-N, and P-I/V-K/R-W-T/M-A-P-E (SEQ ID NO:19). Moreover, see FIG. 1, for a diagram of some additional examples of such sequence motifs. In a preferred embodiment of the PTK/adaptor protein complexes of the invention, the PTK is the receptor PTK HER2. The HER2 tyrosine kinase catalytic domain is well known to those of skill in the art, see, for example, Plowman, G. et al., 1993, Proc. Natl. Acad. Sci. USA 90:1746–1750.

The PTK component of the PTK/adaptor protein complexes of the invention may further include one or more non-catalytic domains, which may include, but are not limited to, one or more SH2 and/or one or more SH3 domains, and/or (in the case of receptor PTKs) a hydrophobic transmembrane domain. An SH2 (i.e., src homology domain 2) non-catalytic domain is generally approximately 100 amino acid residues in length. Such SH2 domains may contain a number of highly conserved or invariant amino acid residues within several, preferably five, well-conserved amino acid sequence motifs, which are well known to those of ordinary skill in the art. See, for example Koch et al. (Koch, A. C., 1991, Science 252:668–674), which is incorporated herein, by reference, in its entirety. For example, the amino acid consensus sequences may include, but are not limited to, F-L-I-R-E-S (SEQ ID NO:20) and F-L-V-R-E-S (SEQ ID NO:21). The R residue of these consensus sequences is invariant among SH2 domains. Such well-conserved amino acid sequences motifs are separated by stretches of more variable amino acid sequence elements, which, while variable, generally contain one or more G or P residues.

An SH3 (i.e., src homology domain 3) non-catalytic domain is approximately 50 amino acids residues in length. While the amino acid sequence within an SH3 domain may be variable, the 3-dimensional, tertiary, structure of the domain is well conserved. Such an SH3 tertiary structure is well known to those of ordinary skill in the art. See, for example, Koyama et al. (Koyama, S. et al., 1993, Cell 72:945–952) which is incorporated herein, by reference, in its entirety.

Intracellular, cytoplasmic PTK components of the PTK/adaptor protein complex of the invention may include, for example, members of the Src family, such as src, yes, fgr, fyn, lyn, hck, lck, and blk; members of the Fes family, such as fes and fer; members of the Abl family, such as abl and arg; and members of the Jak family, such as jak1 and jak2. Transmembrane, receptor PTK components of the PTK/adaptor protein complex of the invention may include, for example, such molecules as members of the FGF receptor, Sevenless/ROS, Insulin receptor, PDGF receptor, and EGF receptor family of growth factor receptors. In a preferred embodiment of the invention, the PTK component of the PTK/adaptor protein complex is the receptor PTK HER2.

The adaptor protein components of the PTK/adaptor protein complexes of the invention comprise one or more SH2 and/or one or more SH3 non-catalytic domains. The SH2 and SH3 domains which may be a part of the adaptor proteins are as described, above, for the PTK components. Adaptor proteins which may be components of the PTK/adaptor protein complexes of the invention, may include, for example, SHC, ISGF3α, and members of the GRB subfamily of proteins, such as GRB-1/p85, GRB-2, GRB-3/c-Crk, GRB-4/Nck, GRB-7, and GRB-10, with GRB-7 being a preferred adaptor protein component of the PTK/adaptor protein complex of the invention. In a preferred embodiment of the invention, the PTK/adaptor protein complex of the invention comprises the receptor PTK HER2 and the adaptor protein GRB-7.

The PTK/adaptor protein complexes of the invention, and/or the individual components of the complexes may be substantially purified utilizing methods which are described below, in Section 5.2.3.1. Further, the PTK and/or adaptor proteins, components of the complexes of the invention, and portions, and/or derivatives of such components may be produced by utilizing a variety of methods which include, but are not limited to, chemical synthesis or recombinant DNA techniques, as described in Section 5.2.3.2, below. Derivatives and methods of derivatization are described in Section 5.2.3.3, below. Additionally cells exhibiting such complexes may be produced via methods such as those described below, in Section 5.2.3.2, below.

5.2 TREATMENT OF PTK/ADAPTOR PROTEIN COMPLEX-RELATED ONCOGENIC DISORDERS

Described in this Section are methods and compositions for the treatment of oncogenic disorders involving a PTK capable of complexing with a member of the SH2- and/or SH3-containing family of adaptor proteins. Examples of such oncogenic disorders may include, but are not limited to, human breast cancer. Specifically, in Section 5.2.1, below, agents are described which are capable of disrupting such complexes. Such agents may be capable of decreasing or inhibiting the interaction between the component PTK and adaptor protein members of the complex of interest, and/or may decrease or inhibit the activity of the PTK/adaptor protein complex of interest. In Section 5.2.2, below, agents are described which are capable of modulating the activity and/or level of one or more of the components of the PTK/adaptor protein complexes. Additionally, in Section 5.2.3, below, methods for the administration of such agents to patients is described.

In a preferred embodiment of the invention, the PTK/adaptor complex which is disrupted or whose activity is decreased or inhibited, or in which the cellular level and/or activity of one or more of the complex components is decreased is one in which the PTK component is the receptor PTK HER2 and the adaptor protein is the adaptor protein GRB-7. Further, the oncogenic disorders which administration of such agents treats in this preferred embodiment include, but are not limited to, human breast cancers.

5.2.1 DISRUPTION OF PTK/ADAPTOR PROTEIN COMPLEXES

Disruption of PTK/adaptor protein complexes, for example by decreasing or inhibiting the interactions between component members such a complex may have differing modulatory effects on the signal transduction event involved, depending on the individual PTK/adaptor protein complex. "Disruption", as used here, is meant to refer not only to a physical separation of PTK/adaptor protein complex components, but also refers to a perturbation of the activity of the PTK/adaptor complexes, regardless of whether or not such complexes remain able, physically, to form. "Activity", as used here, refers to the function the PTK/adaptor protein complex in the signal transduction cascade of the cell in which such a complex is formed, i.e., refers to the function of the complex in effecting or inhibiting the transduction of an extracellular signal into a cell. For example, the effect of complex disruption may augment, reduce, or block the signal normally transduced into the cell. Likewise, depending on the oncogenic disorder involved, either augmentation, reduction, or blockage of the signal normally transduced into the cell will be desirable for the treatment of the disorder.

Taking the HER2/GRB-7 complex as an example, as demonstrated in the Working Example presented in Section 7, below, both the PTK HER2 gene and the adaptor protein GRB-7 gene are often overexpressed in breast cancer cells. Further, it is demonstrated in the Working Example presented in Section 8, below, that HER2 and GRB-7 form a tight PTK/adaptor protein complex in breast cancer cells. The disruption of a HER2 PTK/GRB-7 adaptor protein complex might, therefore, be expected to inhibit the transduction of some quantitatively and/or qualitatively abnormal signal and, thus, prevent and/or reverse the oncogenic transformation of cells, such as those involved in breast cancer, in which the complex forms.

Alternatively, an oncogenic disorder involving a PTK/adaptor complex may, for example, develop because the presence of such a complex brings about the aberrant inhibition of a normal signal transduction event. In such a case, the disruption of the PTK/adaptor complex would allow the restoration of the usual signal transduction event. Further, an aberrant PTK/adaptor complex may bring about an altered subcellular adaptor protein localization, which may result in, for example, dysfunctional cellular events. An inhibition of the PTK/adaptor complex in this case would allow for restoration or maintenance of a normal cellular architecture. Still further, an agent or agents that cause(s) disruption of the PTK/adaptor complex may bring about the disruption of the interactions among other potential components of a complex which comprises a PTK and an adaptor protein.

When considering PTK/adaptor protein complexes wherein the PTK component of the complex is a transmembrane, receptor-type PTK, such as, for example, is the case for the HER2/GRB-7 complex, agents may be administered that act extracellularly to inhibit the receptors or their ligands, and, thus, may directly modulate signal transduction events which may lead to the development of oncogenic disorders. For example, soluble PTKs, peptides representing extracellular PTK domains, or peptides representing those portions of extracellular PTK domains which are known to bind ligands may be administered, using techniques well known to those skilled in the art, that, when exposed to the PTK-expressing cells of interest could act to compete with endogenous transmembrane PTK receptor molecules for available ligands, thus reducing or inhibiting ligand binding to endogenous PTKs. Additionally, antibodies directed against the extracellular portions of such receptor PTKs may be administered which, when bound to the receptor, prohibit ligand binding. Methods which may be utilized for the production of such antibodies are described, below in Section 5.2.1.1. Further, small organic or inorganic molecules may be administered which, for example, bind receptor, making the receptor unable to bind ligand. The effect of any such procedure could bring about a reduction or inhibition of the interaction between the PTK and the adaptor protein, possibly by blocking the autophosphorylation of the PTK, which could, in turn, reduce the affinity of the adaptor protein for the PTK molecule, or, for example, by blocking phosphorylation of the adaptor protein of complex by the PTK of the complex.

In addition, again when considering receptor-type PTKs, extracellular molecules which bind to such PTKs may be administered, using techniques well known to those in the art, which, while binding the PTK, do not activate the molecule. Extracellular molecules of this type may be composed, for example, of modified forms of a native ligand for the PTK of interest or may be composed of a small organic or inorganic molecule that mimics ligand binding, such that receptor binding may still occur, but activation of the kinase does not. A molecule with such a design could act in much the same way that administration of soluble PTK would, in that both procedures could have the final effect of reducing or inhibiting the formation of the PTK/adaptor protein complexes and/or the interaction between the components of the PTK/adaptor protein complexes.

Still further, molecules which are capable of binding native ligands of the receptor PTKs of the PTK/adaptor complexes of the invention may be administered, using techniques well known to those of skill in the art. Molecules in this class would act to inhibit the ligands' ability to bind the PTK receptor, and thus could have the final effect of reducing or inhibiting the formation and/or activity of PTK/adaptor protein complexes. Such molecules may include, for example, small organic or inorganic molecules which bind ligand, making the ligand unavailable for receptor binding. Alternatively, antibodies directed against the ligand for the receptor of interest may be administered such that the ligand, when bound by antibody, is unable to bind to the receptor. Methods which may be used for the production of such antibodies are described below, in Section, 5.2.1.1.

Using the HER2/GRB-7 complex as an example, 20 agents which act extracellularly to disrupt the complex may include, for example the tyrphostins, examples of which may be found in Osherov, N. et al., 1993, J. Biol. Chem. 268:11134–11142.

Agents which act intracellularly to directly interfere with the formation and/or activity of the PTK/adaptor complexes of the invention may also be administered for the treatment of oncogenic disorders, such as breast cancer. Such agents may include, but are not limited to, peptides and/or phosphopeptides comprising SH2 and or SH3 domains, or SH2 and/or SH3-binding domains, which would act to compete with the components of the PTK/adaptor complexes for binding, thus reducing or inhibiting the formation of complexes, which would, in turn, reduce or inhibit the development of the oncogenic disorder of interest.

SH2 and SH3 peptide domains are as described, above, in Section 5.1. SH2-binding peptide domains are well known in the art. See, for example, Songyang, S. et al. (Songyang, S. et al., 1993, Cell 72:767–778), Rotin et al. (Rotin, D. et al., EMBO J. 11:559–567), and Skolnick et al. (Skolnick, E. Y. et al., 1993, EMBO J. 12:1929–1936), which are incorporated herein, by reference, in their entirety. SH2 domains may exhibit a specificity for certain SH2-binding domains. For example, SH2-binding peptide domains may include, but are not limited to a phosphoTyr-hydrophilic-hydrophilic-Ile/Pro amino acid sequence motif (generally, such a sequence motif is preferred for SH2 domains of the type found in, for example, the src, fyn, lck, fgr, abl, crk, and nck proteins), and phosphoTyr-hydrophobic-X-hydrophobic, and/or phosphotyr-Met-X-Met (generally, such sequence motifs are preferred for SH2 domains of the type found in, for example, p85, phospholipase C-γ, and SHPTP2 proteins). Further, a consensus sequence developed from the analysis of the domains of several proteins that bind the SH2 domains of the GRB-2 protein has been determined to be X-P-X-Y-V/I-N-V/I (SEQ ID NO:15). The tyrosine (Y) residue of such a consensus sequence is preferably phosphorylated. In addition, SH2-binding peptide domains may comprise regions rich in Ser and Thr residues some or all of which are phosphorylated (Pendergast, A. M. et al., 1991, Cell 66:161–171).

SH-2-binding domains may be identified by a variety of techniques. (See for example, Pawson, T. and Schlessinger, J., 1993, Current Biology 3:434–442, which is herein incorporated, by reference, in its entirety.) Such techniques may include, for example, identifying peptide sequences that have consequences such as those described above. Additionally, SH2-binding domains may be identified by an affinity chromatography method that utilizes a degenerate peptide library containing phosphotyrosine amino acid residues. Such a library may be constructed by following, for example, the methods described in Songyang, Z. et al., 1993, Cell 72:767–778. Utilizing this technique, briefly, the library is exposed to immobilized SH2 domains for a time sufficient to allow binding of members of the peptide library to the SH2 domains. Second, the unbound members of the peptide library are removed from the immobilized SH2 domains. Third, the bound peptide library members are eluted from the SH2 domains and identified, thus identifying potential SH2-binding peptides.

SH3-binding peptide domains are also well known to those of ordinary skill in the art. See, for example, Ren et al. (R. et al., 1993, Science 259:1157–1161) and Cicchetti et al. (Cicchetti, P. et al., 1992, Science 257:803–806), which are incorporated herein, by reference, in their entirety. Such SH3-binding peptide domains are generally rich in proline amino acid residues, although amino acid residues in addition to solely proline are also critical for SH3 binding. One possible consensus sequence for a SH3-binding domain is: X-P-X-X-P-P-P-hydrophobic residue-X-P (SEQ ID NO:16). Further, the SH3 domains of the GRB-2 member of the adaptor family of molecules have been determined to be P-P-V-P-P-R-R (SEQ ID NO:17), an amino acid sequence motif found in the SOS protein.

Nucleotide sequences encoding peptide agents which are to be utilized intracellularly may be expressed in the cells of interest, using compositions and techniques which are well known to those of ordinary skill in the art. Peptide agents encoded may include, for example, adaptor protein SH2 domains, such as the SH2 domain of GRB-7, PTK SH2-binding domains such as the SH2-binding domain of HER2, and/or mutant forms of adaptor and/or PTK proteins. A mutant adaptor protein such as a mutant GRB-7, may for example, be expressed which retains the ability to bind a PTK, such as, for example, HER2 but lacks signal transduction activity. Compositions and techniques for expression may include, for example, expression vectors derived from viruses such as retroviruses, vaccinia virus, adenoviruses, adeno-associated virus, herpes viruses, or bovine papilloma virus, may be used for delivery and expression of such nucleotide sequences into the targeted cell population. Methods for the construction of such vectors are well known. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y. SH2-binding domains can be identified using, for example, techniques such as those described in Rotin et al. (Rotin, D. et al., EMBO J. 11:559–567), Songyang et al. (Songyang, S. et al., 1993, Cell 72:767–778), Felder, S. et al., 1993, Mol. Cell. Biol. 13:1449–1455, Fantl, W. J. et al., 1992, Cell 69:413–422, and Domchek, S. M. et al., 1992, Biochemistry 31:9865–9870).

Alternatively, antibodies capable of interfering with PTK/adaptor complex formation may be administered for the treatment of oncogenic disorders involving a PTK capable of forming a complex with an adaptor protein. For example, neutralizing antibodies which are capable of interfering with ligand binding to receptor type PTKs may be administered using techniques such as those described above. The effect of such an administration would be similar to that described, above, for the administration of soluble PTKs. Additionally, single chain neutralizing antibodies which bind to intracellular epitopes to effect a disruption of PTK/adaptor complex formation may also be administered. Such single chain antibodies may be administered, for example, nucleotide sequences encoding single-chain antibodies may be expressed within the target cell population by utilizing, for example, techniques such as those described in Marasco et al. (Marasco, W. et al., 1993, Proc. Natl. Acad. Sci. USA 90:7889–7893). Methods which may be used for the production of such antibodies are described, below, in Section 5.2.2.1.

Agents which act intracellularly to interfere with the formation and/or activity of the PTK/adaptor protein complexes of the invention may also be small organic or inorganic compounds. Examples of such molecules may be found, for example, in Gazit, A. et al., 1989, J. of Medicinal Chem. 32:2344–2352; Lyall, R. et al., 1989, J. Biol. Chem. 264:14503–14509; and U.S. Pat. Nos. 5,196,446 and 5,217, 999. A method for identifying these and other intracellular agents is described in the Working Example presented, below, in Section 11.

5.2.1.1 ANTIBODIES TO PTK/ADAPTOR COMPLEXES

Described herein are methods for the production of antibodies which are capable of specifically recognizing a PTK/adaptor complex or an epitope thereof, or of specifically recognizing an epitope on either the PTK or adaptor components of the complex, especially those epitopes which would not be recognized by the antibody when the PTK and/or adaptor component is present separate and apart from the PTK/adaptor complex. Such antibodies may include, but are not limited to polyclonal antibodies, monoclonal antibodies (mAbs), humanized or chimeric antibodies, single chain antibodies, Fab fragments, F(ab')$_2$ fragments, fragments produced by a FAb expression library, anti-idiotypic (anti-Id) antibodies, and epitope-binding fragments of any of the above. Such antibodies may be used, for example, in the detection of a PTK/adaptor complex in a biological sample, or, alternatively, as a method for the inhibition of PTK/adaptor complex formation, thus, inhibiting the development of an oncogenic disorder.

Polyclonal antibodies are heterogeneous populations of antibody molecules derived from the sera of animals immunized with an antigen, such as PTK/adaptor complex, or an antigenic functional derivative thereof. For the production of polyclonal antibodies, various host animals may be immunized by injection with the PTK/adaptor complex including but not limited to rabbits, mice, rats, etc. Various adjuvants may be used to increase the immunological response, depending on the host species, including but not limited to Freund's (complete and incomplete), mineral gels such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

A monoclonal antibody, which is a substantially homogeneous population of antibodies to a particular antigen, may be obtained by any technique which provides for the production of antibody molecules by continuous cell lines in culture. These include, but are not limited to the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 31:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce PTK/adaptor complex-specific single chain antibodies. Single chain antibodies are formed by linking the heavy and light chain fragment of the Fv region via an amino acid bridge, resulting in a single chain polypeptide.

Antibody fragments which contain specific binding sites of a PTK/adaptor complex may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity to the PTK/adaptor complex.

5.2.2 MODULATION OF ACTIVITY AND/OR LEVEL OF PTK/ADAPTOR COMPLEX COMPONENTS

One or more components of a PTK/adaptor protein complex may be present at a higher than normal cellular level (i.e., higher than the concentration known to usually be present in the cell type exhibiting the PTK/adaptor protein complex of interest) and/or may exhibit an abnormally increased level of cellular activity (ie., greater than the activity known to usually be present in the cell type exhibiting the PTK/adaptor protein complex of interest). For example, the gene encoding a PTK/adaptor protein complex component may begin to be overexpressed, or may be amplified (i.e., its gene copy number may be increased) in certain cells, leading to an increased number of component molecules within these cells. Additionally, a gene encoding a PTK/adaptor protein complex component may begin to express a modified protein product that exhibits a greater than normal level of activity. "Activity", here, refers to the normal cellular function of the component, either enzymatic e.g., kinase activity, or structural, as in the case of adaptor proteins, whose function may include, for example, bringing two or more cellular molecules into the appropriate proximity.

Such an increase in the cellular level and/or activity of a PTK/adaptor protein complex may lead to the development of an oncogenic disorder. This appears to be the case, for example, with the HER2/GRB-7 protein complex, in which HER2 and GRB-7 are often seen to be co-overexpressed in breast cancer cells, as demonstrated in the Working Example presented, in Section 7, below. Treatment of oncogenic disorders, such as breast cancer in the case of the HER2/GRB-7 complex, may, therefore, be effectuated by the administration of agents which decrease the cellular level and/or the activity of the overexpressed and/or overactive PTK/adaptor protein complex component.

Techniques for decreasing the cellular level and/or the activity of one or more of the PTK/adaptor protein complex components of interest may include, but are not limited to antisense or ribozyme approaches, and/or gene therapy approaches, each of which is well known to those of skill in the art, as described, below, in Sections 5.2.2.1–5.2.2.2.

5.2.2.1 ANTISENSE AND RIBOZYME APPROACHES

Included in the scope of the invention are oligoribonucleotides, including antisense RNA and DNA molecules and ribozymes that function to inhibit translation of one or more components of a PTK/adaptor protein complex. Anti-sense RNA and DNA molecules act to directly block the translation of mRNA by binding to targeted mRNA and preventing protein translation. With respect to antisense DNA, oligodeoxyribonucleotides derived from the translation initiation site, e.g., between −10 and +10 regions of the PTK nucleotide sequence of interest, are preferred. In the case of GRB-7, for example, this sequence would correspond to nucleotides 359 through 379 of the GRB-7 DNA sequence.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of RNA sequences encoding PTK/adaptor protein complex components.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate targets may also be evaluated by testing their accessibility to hybridization with complementary oligonucleotides, using ribonuclease protection assays.

Both anti-sense RNA and DNA molecules and ribozymes of the invention may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

5.2.2.3 GENE THERAPY

Target cell populations may be modified by introducing altered forms of one or more components of the PTK/adaptor protein complexes in order to modulate the activity of such complexes. For example, as demonstrated in the Working Example presented, below, in Section 8, the adaptor protein GRB-7 and/or the receptor PTK HER2 are overexpressed in breast cancer cells. By reducing or inhibiting HER2 and/or GRB-7 activity within target cells, the abnormal signal transduction event(s) leading to oncogenic transformation may be decreased, inhibited, or reversed. Deletion or missense mutants of a PTK, such as HER2, or an adaptor protein, such as GRB-7, that retain the ability to interact with other components of the PTK/adaptor protein complexes but cannot function in signal transduction may be used to inhibit an abnormal, deleterious signal transduction event.

Expression vectors derived from viruses such as retroviruses, vaccinia virus, adenovirus, adeno-associated virus, herpes viruses, or bovine papilloma virus, may be used for delivery of nucleotide sequences encoding recombinant PTK/adaptor protein complex components into the targeted cell population. Methods which are well known to those skilled in the art can be used to construct recombinant viral vectors containing PTK coding sequences. See, for example, the techniques described in Maniatis et al., 1989, Molecular Cloning: A Laboratory Manual, Cold Spring Harbor Laboratory, N.Y. and Ausubel et al., 1989, Current Protocols in Molecular Biology, Greene Publishing Associates and Wiley Interscience, N.Y. Alternatively, recombinant nucleic acid molecules encoding PTK and/or adaptor protein sequences can be used as naked DNA or in reconstituted system e.g., liposomes or other lipid systems for delivery to target cells (See e.g., Felgner et al., 1989, Nature 337:387–388).

5.2.3 PHARMACEUTICAL FORMULATIONS, DOSAGES AND MODES OF ADMINISTRATION

The particular compound, antibody, antisense or ribozyme molecule that affects the PTK/adaptor protein complexes and the oncogenic disorders of interest can be administered to a patient either by themselves, or in pharmaceutical compositions where it is mixed with suitable carriers or excipient(s).

In treating a patient exhibiting an oncogenic disorder of interest, a therapeutically effective amount of a agent or agents such as these is administered. A therapeutically effective dose refers to that amount of the compound sufficient to result in amelioration of symptoms or a prolongation of survival in a patient. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. The data obtained from these cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal disruption of the PTK/adaptor protein complex, or a half-maximal inhibition of the cellular level and/or activity of a complex component) as determined in cell culture. Such information can be used to more accurately determine useful doses in humans. Levels in plasma may be measured, for example, by high performance liquid chromatography (HPLC).

The exact formulation, route of administration and dosage can be chosen by the individual physician in view of the patient's condition. (See e.g. Fingl et al., 1975, in "The Pharmacological Basis of Therapeutics", Ch. 1 p1).

It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and to the route of administration. The severity of the condition may, for example, be evaluated, in part, by such prognostic evaluation methods as are described, below, in Section 5.5. Further, the dose and perhaps dose frequency, will also vary according to the age, body weight, and response of the individual patient. A program comparable to that discussed above may be used in veterinary medicine.

Depending on the specific conditions being treated, agents may be formulated and administered systemically or locally. Techniques for formulation and administration may be found in "Remington's Pharmaceutical Sciences," 1990, 18th ed., Mack Publishing Co., Easton, Pa. Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

5.3 IDENTIFICATION OF AGENTS FOR TREATMENT OF ONCOGENIC DISORDERS

The PTK/adaptor complexes, components of such complexes, functional equivalents thereof, and/or cell lines that express such components and exhibit such PTK/adaptor protein complexes may be used to screen for additional compounds, antibodies, or other molecules capable of modulating the signal transduction event in which such complexes are involved. Methods for purifying and/or producing such PTK/adaptor complexes, components of the complexes, functional equivalents thereof, and/or cell lines are described, below, in Section 5.3.2. The compounds, antibodies, or other molecules identified may, for example, act to disrupt the PTK/adaptor protein complexes of the invention (i.e., decrease or inhibit interactions between component members of the complexes, thereby causing physical separation of the components, and/or perturbing the activity of the PTK/adaptor complexes) or may lower the cellular level and/or decrease the activity of one or more of the components of such complexes. Such compounds may include, but are not limited to, peptides made of D- and/or L-configuration amino acids (in, for example, the form of random peptide libraries; see Lam, K. S. et al., 1991, Nature 354:82–84), phosphopeptides (in, for example, the form of random or partially degenerate, directed phosphopeptide libraries; see, for example, Songyang, Z. et al., 1993, Cell 72:767–778), antibodies, and small organic or inorganic molecules. Synthetic compounds, natural products, and other sources of potentially biologically active materials may be screened in a variety of ways, as described in this Section. The compounds, antibodies, or other molecules identified may be used as oncogenic disorder treatments, as described above in Section 5.2.1.

Compounds that bind to individual components, or functional portions of the individual components of the receptor PTK/adaptor complexes (and may additionally be capable of disrupting complex formation) may be identified. Such compounds may then be tested for an ability to modulate an oncogenic disorder involving the complex.

In one embodiment of such method is a method for identifying a compound to be tested for an ability to modulate an oncogenic disorder involving a receptor PTK polypeptide/adaptor polypeptide complex comprising:

(a) exposing at least one compound to a peptide comprising a functional portion of a member of the receptor protein tyrosine kinase polypeptide/adaptor polypeptide complex for a time sufficient to allow binding of the compound to the functional portion of the member;

(b) removing non-bound compounds; and (c) determining the presence of the compound bound to the functional portion of the member of the receptor protein tyrosine kinase polypeptide/adaptor polypeptide complex, thereby identifying an agent to be tested for an ability to modulate an oncogenic disorder involving a protein tyrosine kinase polypeptide/adaptor polypeptide complex.

A functional portion of an individual component of the complexes may be defined here as a peptide portion of an individual component of a complex capable of forming a stable complex with another member of the complex under standard cellular and physiological conditions. For example, a functional portion of a PTK may include, but is not limited to, a peptide portion of the SH2-binding domain of the PTK which is still capable of stably binding an SH2 domain of an adaptor protein, and thus is still capable of forming a complex with that adaptor protein. Further, in the case of the catalytic domains of the individual PTK components of the invention, a functional portion of a catalytic domain may refer to a peptide still capable of stably binding a substrate molecule under standard physiological conditions. In the case of the receptor PTK components of the PTK/adaptor protein complexes of the invention, a functional portion of this component may be defined as any portion of the extracellular domain of the receptor PTK of at least about 4 amino acids in length. Such portions may include, but are not limited to, regions of the receptor PTK extracellular domains capable of binding a ligand of the receptor PTK.

One method utilizing this approach that may be pursued in the isolation of such receptor PTK/adaptor protein complex component-binding molecules would include the attachment of a component molecule, or a peptide comprising a functional portion thereof, to a solid matrix, such as, for example, agarose or plastic beads, microtiter plate wells, petri dishes, or membranes composed of, for example, nylon or nitrocellulose, and the subsequent incubation of the attached component molecule in the presence of a potential component-binding compound or compounds. After incubation, unbound compounds are washed away, component-bound compounds are recovered. By utilizing this procedure, large numbers of types of molecules may be simultaneously screened for PTK/adaptor protein complex component-binding activity.

The PTK/adaptor protein complex components which may be utilized in the above screening method may include, but are not limited to, PTK molecules or peptides comprising functional portions thereof, such as PTK catalytic domains, phosphorylation domains, SH2 domains, SH3 domains, SH2-binding domains, SH3-binding domains, extracellular domains, or portions of extracellular domains, such as ligand-binding domains, and adaptor proteins, or functional portions thereof, such as SH2 domains and SH3 domains. The peptides used may be phosphorylated, e.g., may contain at least one phosphorylated amino acid residue, preferably a phosphorylated Tyr amino acid residue, or may be unphosphorylated. A phosphorylation domain may be defined as a peptide region that is specifically phosphorylated at certain amino acid residues. A functional portion of such a phosphorylation domain may be defined as a peptide capable of being specifically phosphorylated at certain amino acids by a specific PTK. A functional portion of an SH2 domain may be defined as a peptide comprising at least a portion of an SH2 domain which is capable of specifically binding an SH2-binding domain. Likewise, a functional portion of an SH3 domain may be defined as a peptide comprising at least a portion of an SH3 domain which is capable of specifically binding an SH3-binding domain. A functional portion of an SH2-binding domain may be defined as a peptide capable of binding an SH2 domain, and may be at least about 4 amino acid residues in length. A functional portion of an SH3-binding domain may be defined as a peptide capable of binding an SH3 domain, and may be at least about 4 amino acids in length, with a length of about 10 amino acid residues being preferred.

Further, compounds may be screened for an ability to inhibit the formation of or, alternatively, disrupt PTK/adaptor protein complexes. Such compounds may then be tested for an ability to modulate an oncogenic disorder involving the complex of interest. For example, in vitro complex formation may be assayed by, first, immobilizing one component, or a peptide comprising a functional portion thereof, of the complex of interest to a solid support. Second, the immobilized complex component may be exposed to a compound such as, for example, one identified as above, and to a second component, or a peptide comprising a functional portion thereof, of the complex of interest, capable of forming a complex with the immobilized complex component or functional portion thereof. Third, it may be determined whether or not the second component is still capable of forming a complex with the immobilized component in the presence of the compound. A method such as this is described in the Example presented in Section 11, below.

Alternatively, compounds may be screened for an ability to disrupt receptor PTK/adaptor protein complexes. For example, a compound may be exposed to a receptor PTK/adaptor protein complex for a time sufficient to allow disruption of the complex, and the disruption of the complex may then be assayed by any of a variety of techniques well known to those of skill in the art. The compound may also be exposed to a peptide comprising a one member of a receptor PTK/adaptor protein complex bound to a peptide comprising a functional portion of a second member of the complex. Assays which may be utilized to detect complex disruption may include, but are not limited to, co-immunoprecipitation, wherein it is determined whether immunoprecipitation utilizing an antibody directed against one member of the receptor PTK/adaptor protein complex of interest simultaneously functions to precipitate not only the component it is directed to but also other components of the complex. If the complex has remained intact, the complex will be precipitated. If disruption of the receptor PTK/adaptor protein complex has occurred, only the component the antibody is directed against will be precipitated.

Additionally, in vivo complex formation and/or disruption may be assayed by utilizing techniques well known to those of skill in the art which include, but are not limited to co-immunoprecipitation techniques. Briefly, a cell line capable of forming a PTK/adaptor complex of interest may be exposed to a compound such as one identified as above, and a cell lysate may be prepared from this exposed cell line. An antibody raised against one of the components of the complex of interest may be added to the cell lysate, and subjected to standard immunoprecipitation techniques. In cases where a complex is still formed, (or is not disrupted), the immunoprecipitation will precipitate the complex, whereas in cases where the complex has not been formed (or has been disrupted), only the complex component to which the antibody is raised will be precipitated. Compounds identified may then be tested to modulate an oncogenic disorder including the receptor PTK/adaptor complex of interest.

In one embodiment of such a method of assaying in vivo complex formation and/or complex disruption is a method for identifying a compound to be tested for an ability to modulate an oncogenic disorder involving a receptor protein tyrosine kinase polypeptide/adaptor polypeptide complex comprising:

(a) contacting the compound to a cell capable of forming a receptor tyrosine kinase polypeptide/adaptor polypeptide complex for a time sufficient to allow binding of the compound to the receptor protein tyrosine kinase polypeptide of the receptor protein tyrosine kinase polypeptide/adaptor polypeptide complex;

(b) detecting the level of receptor protein tyrosine kinase polypeptide/adaptor polypeptide complex present in the cell of step (a);

(c) detecting the level of receptor protein tyrosine kinase polypeptide/adaptor polypeptide complex present in a cell of the type in step (a) that has not contacted the compound; and (d) comparing the level of receptor protein tyrosine kinase polypeptide/adaptor polypeptide complex detected in step (b) to the level detected in step (c), so that if the level detected in step (c) is greater than the level detected in step (b), a compound to be tested for an ability to modulate an oncogenic disorder involving a receptor protein tyrosine kinase polypeptide/adaptor polypeptide complex is identified.

The ability of a compound to modulate the transformation capability, and thus, to assay the compound's ability to modulate an oncogenic disorder, of the receptor PTK/adaptor protein complex of interest may be directly assayed. Such compounds may, but are not required to, include those agents identified by utilizing the above screening technique. For example, a compound or compounds may be administered to a cell such as a breast cancer cell, capable of forming a receptor PTK/adaptor complex, a HER2/GRB-7 complex, for example, which, in the absence of any inhibitory agent, would lead to the cell's transformation. The transformation state of the cell may then be measured in vitro, by monitoring, for example, its ability to form colonies in soft agar. Alternatively, a cell's transformation state may be monitored in vivo by, for example, determining its ability to form tumors in immunodeficient nude or severe combined immunodeficiency (SCID) mice. Compounds identified that, for example, reduce the cell's ability to form colonies in soft agar and/or form tumors in such mice are capable of modulating the transformation capability of the receptor PTK/adaptor protein complex of interest.

Compounds capable of disrupting receptor PTK/adaptor complexes and/or formation, and, further disrupting complex formation capable of reducing or inhibiting oncogenic disorders, such as breast cancer, which involve the formation of such complexes may be used in the treatment of patients exhibiting or at risk for such disorders. A sufficient compound or compounds such as those described above may be administered to a patient so that the oncogenic capability of cells which, in the absence of compounds, would contain the receptor PTK/adaptor protein complexes involved in the oncogenic disorder of interest, is reduced or eliminated. Techniques which may be used to administer such compounds and formulations containing such compounds are described, above, in Section 5.2.3, above.

5.3.2 PURIFICATION AND PRODUCTION OF PTK/ADAPTOR COMPLEXES

Described in this Section are methods for the synthesis or recombinant expression of components, or fragments thereof, of the PTK/adaptor protein complexes of the invention. Also described herein are methods by which cells exhibiting the PTK/adaptor protein complexes of the invention may be engineered.

5.3.2.1 PURIFICATION METHODS

The PTK/adaptor complexes of the invention may be substantially purified, i.e., may be purified away from at least 90% (on a weight basis), and from at least 99%, if desired, of other proteins, glycoproteins, and other macromolecules with which it is associated. Such purification can be achieved by utilizing a variety of procedures well known to those of skill in the art, such as subjecting cells, tissue or fluid containing the PTK/adaptor complex to a combination of standard methods, which include, but are not limited to, ammonium sulfate precipitation, molecular sieve chromatography, and/or ion exchange chromatography. Alternatively, or additionally, a PTK/adaptor complex may be purified by immunoaffinity chromatography using an immunoadsorbent column to which an antibody is immobilized which is capable of binding to one or more components of the PTK/adaptor complex. Such an antibody may be monoclonal or polyclonal in origin. Other useful types of affinity purification for the PTK/adaptor protein complex may utilize, for example, a solid-phase substrate which binds the catalytic kinase domain of a PTK, or an immobilized binding site for noncatalytic domains of the PTK and/or adaptor components of the complex, which bind in such a manner as to not disrupt the complex.

The PTK/adaptor complex of the present invention may be biochemically purified from a variety of cell or tissue sources. For purification of a naturally occurring PTK/adaptor complex, cellular sources may include, for example, baculovirus-infected SF9 cells, A-431, CHO, and/or 3T3 cells. In a preferred embodiment of the present invention, the PTK/adaptor complex comprises the receptor PTK HER2 and the GRB-7 adaptor protein. Sources for the purification of such a HER2/GRB-7 complex may include, but are not limited to the SKBR-3 cell line (ATCC HTB30). Other sources could include, for example, BT474 (ATCC HTB20) cells, a cell line transfected with nucleotide sequences to express both HER-2 and GRB-7, ZR-75-30 (ATCC CRL1504) cells, MDA-MB-453 (ATCC HTB27) cells, or tumors extracted from transgenic mice expressing both GRB-7 and HER-2.

5.3.2.2 SYNTHESIS AND EXPRESSION METHODS

Methods for the synthesis of polypeptides or fragments thereof, which are capable of acting as components of the PTK/adaptor complexes of the present invention, are well-known to those of ordinary skill in the art. See, for example, Creighton, 1983, Proteins: Structures and Molecular Principles, W. H. Freeman and Co., N.Y., which is incorporated herein, by reference, in its entirety.

Components of a PTK/adaptor complex which have been separately synthesized or recombinantly produced, may be reconstituted to form a complex by standard biochemical techniques well known to those skilled in the art. For example, samples containing the components of the PTK/adaptor complex may be combined in a solution buffered with greater than about 150 mM NaCl, at a physiological pH in the range of 7, at room temperature. For example, a buffer comprising 20 mM Tris-HCl, pH 7.4, 137 mM NaCl, 10% glycerol, 1% Triton X-100, 0.1% SDS, 0.5% deoxycholate and 2 mM EDTA could be used.

Methods for preparing the components of PTK/adaptor complexes of the invention by expressing nucleic acid encoding PTK and/or adaptor proteins are described herein. Methods which are well known to those skilled in the art can be used to construct expression vectors containing PTK and/or adaptor protein coding sequences and appropriate transcriptional/translational control signals. These methods include, for example, in vitro recombinant DNA techniques, synthetic techniques and in vivo recombination/genetic recombination. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y. DNA and RNA synthesis may, additionally, be performed using an automated synthesizers. See, for example, the techniques described in "Oligonucleotide Synthesis", 1984, Gait, M. J. ed., IRL Press, Oxford.

A variety of host-expression vector systems may be utilized to express the coding sequences of the components of the PTK/adaptor complexes of the invention. Such host-expression systems represent vehicles by which the coding sequences of interest may be produced, but also represent cells which may, when transformed or transfected with the appropriate nucleotide coding sequences, exhibit the PTK/adaptor protein complexes of the invention. These include but are not limited to microorganisms such as bacteria (e.g., E. coli, B. subtilis) transformed with recombinant bacteriophage DNA, plasmid DNA or cosmid DNA expression vectors containing PTK or adaptor protein coding sequences; yeast (e.g. Saccharomyces, Pichia) transformed with recombinant yeast expression vectors containing the PTK and/or adaptor protein coding sequences; insect cell systems infected with recombinant virus expression vectors (e.g., baculovirus) containing the PTK and/or adaptor protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the PTK and/or adaptor protein coding sequences coding sequence; or mammalian cell systems (e.g. COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the PTK/adaptor complex being expressed. For example, when large quantities of PTK/adaptor complex proteins are to be produced for the generation of antibodies or to screen peptide libraries, vectors which direct the expression of high levels of fusion protein products that are readily purified may be desirable. Such vectors include, but are not limited, to the E. coli expression vector pUR278 (Ruther et al., 1983, EMBO J. 2:1791), in which the PTK and/or adaptor protein coding sequence may be ligated individually into the vector in frame with the lac Z coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned PTK and/or adaptor protein can be released from the GST moiety.

In an insect system, Autographa californica nuclear polyhedrosis virus (AcNPV) is used as a vector to express foreign genes. The virus grows in Spodoptera frugiperda cells. The PTK/adaptor complex coding sequence may be cloned individually into non-essential regions (for example the polyhedrin gene) of the virus and placed under control of an AcNPV promoter (for example the polyhedrin promoter). Successful insertion of the PTK/adaptor complex coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (E.g., see Smith et al., 1983, J. Viol. 46:584; Smith, U.S. Pat. No. 4,215,051).

In mammalian host cells, a number of viral based expression systems may be utilized. In cases where an adenovirus is used as an expression vector, the PTK/adaptor complex coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing PTK and/or adaptor proteins in infected hosts. (E.g., See Logan & Shenk, 1984, Proc. Natl. Acad. Sci. USA 81:3655–3659). Specific initiation signals may also be required for efficient translation of inserted PTK and/or adaptor coding sequences. These signals include the ATG initiation codon and adjacent sequences. In cases where an entire PTK or adaptor protein gene, including its own initiation codon and adjacent sequences, is inserted into the appropriate expression vector, no additional translational control signals may be needed. However, in cases where only a portion of the PTK or adaptor coding sequence is inserted, exogenous translational control signals, including the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, etc.

For long-term, high-yield production of recombinant proteins, stable expression is preferred. For example, cell lines which stably coexpress both the PT and adaptor protein may be engineered. Rather than using expression vectors which contain viral origins of replication, host cells can be transformed with the PTK and adaptor protein DNA independently or coordinately controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which coexpress both the PTK and adaptor protein. Such engineered cell lines are particularly useful in screening and evaluation of compounds that affect signals mediated by the complexes.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes.

New members of the PTK and/or adaptor protein families capable of forming the complexes of the invention may be identified and isolated by molecular biological techniques well known in the art. For example, a previously unknown PTK or adaptor protein gene may be isolated by performing a polymerase chain reaction (PCR; the experimental embodiment set forth by Mullis, K. B., 1987, U.S. Pat. No.

4,683,202) using two degenerate oligonucleotide primer pools designed on the basis of highly conserved sequences within domains common to members of the PTK or adaptor protein family. The template for the reaction may be cDNA obtained by reverse transcription of mRNA prepared from cell lines or tissue known to express PTK/adaptor complexes. The PCR product may be subcloned and sequenced to insure that the amplified sequences represent the sequences of a member of the PTK or adaptor subfamily. The PCR fragment may then be used to isolate a full length PTK or adaptor protein cDNA clone by radioactively labeling the amplified fragment and screening a bacteriophage cDNA library. Alternatively, the labeled fragment may be used to screen a genomic library. For a review of cloning strategies which may be used, see e.g., Maniatis, 1989, Molecular Cloning, A Laboratory Manual, Cold Springs Harbor Press, N.Y.; and Ausubel et al., 1989, Current Protocols in Molecular Biology, (Green Publishing Associates and Wiley Interscience, N.Y.).

A well known, general method for cloning previously unknown adaptor proteins has been described by Skolnik (Skolnik, E. Y., 1991, Cell 65:75) and Skolnik et al., (U.S. patent application Ser. No. 07/643,237) which are incorporated herein, by reference, in their entirety. Briefly, new members of the adaptor family of proteins may be identified by their ability to specifically bind to at least a portion of a tyrosine-phosphorylated peptide comprising an adaptor-protein-binding region. Such a region may include, but is not limited to an SH2-binding domain.

5.3.2.3 DERIVATIVES OF PTK/ADAPTOR COMPLEXES

Also provided herein are functional derivatives of a PTK/adaptor complex. By "functional derivative" is meant a "chemical derivative," "fragment," "variant," "chimera," or "hybrid" of the PTK/adaptor complex, which terms are defined below. A functional derivative retains at least a portion of the function of the PTK or adaptor protein, for example reactivity with an antibody specific for the PTK/adaptor complex, PTK enzymatic activity or binding activity mediated through noncatalytic domains, which permits its utility in accordance with the present invention.

A "chemical derivative" of the PTK/adaptor complex contains additional chemical moieties not normally a part of the protein. Covalent modifications of the protein complex or peptides are included within the scope of this invention. Such modifications may be introduced into the molecule by reacting targeted amino acid residues of the peptide with an organic derivatizing agent that is capable of reacting with selected side chains or terminal residues, as described below.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect or reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine ε-amino group.

Tyrosyl residues are well-known targets of modification for introduction of spectral labels by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction carbodiimide (R'-N-C-N-R') such as 1-cyclohexyl-3-(2-morpholinyl(4-ethyl) carbodiimide or 1-ethyl-3-(4-azonia-4,4-dimethylpentyl) carbodiimide. Furthermore, aspartyl and glutamyl residue are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful, for example, for cross-linking the component peptides of the PTK/adaptor complexes to each other or the PTK/adaptor receptor complex to a water-insoluble support matrix or to other macromolecular carriers. Commonly used cross-linking agents include, for example, 1,1-bis(diazoacetyl)-2-phenylethane, glutaraldehyde, N-hydroxysuccinimide esters, for example, esters with 4-azidosalicylic acid, homo-bifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[p-azidophenyl) dithiolpropioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (Creighton, T. E., Proteins: Structure and Molecular Properties, W.H. Freeman & Co., San Francisco, pp. 79–86 (1983)), acetylation of the N-terminal amine, and, in some instances, amidation of the C-terminal carboxyl groups.

Such derivatized moieties may improve the stability, solubility, absorption, biological half life, and the like. The moieties may alternatively eliminate or attenuate any undesirable side effect of the protein complex and the like. Moieties capable of mediating such effects are disclosed, for example, in Remington's Pharmaceutical Sciences, 18th ed., Mack Publishing Co., Easton, Pa. (1990).

The term "fragment" is used to indicate a polypeptide derived from the amino acid sequence of the PTK or adaptor proteins, of the PTK/adaptor complexes having a length less than the full-length polypeptide from which it has been derived. Such a fragment may, for example, be produced by proteolytic cleavage of the full-length protein. Preferably, the fragment is obtained recombinantly by appropriately modifying the DNA sequence encoding the PTK or adaptor proteins to delete one or more amino acids at one or more sites of the C-terminus, N-terminus, and/or within the native sequence. Fragments of a PTK or adaptor protein, when present in a complex resembling the naturally occurring PTK/adaptor complex, are useful for screening for compounds that act to modulate signal transduction, as described below. It is understood that such fragments, when present in a complex may retain one or more characterizing portions of the native PTK/adaptor complex. Examples of such retained characteristics include: catalytic activity; substrate specificity; interaction with other molecules in the intact cell; regulatory functions; or binding with an antibody specific for the native PTK/adaptor complex, or an epitope thereof.

Another functional derivative intended to be within the scope of the present invention is a PTK/adaptor complex comprising at least one "variant" polypeptide (e.g., PTK or adaptor) which either lack one or more amino acids or contain additional or substituted amino acids relative to the native polypeptide. The variant may be derived from a naturally occurring PTK/adaptor complex component by appropriately modifying the PTK and/or adaptor protein DNA coding sequence to add, remove, and/or to modify codons for one or more amino acids at one or more sites of the C-terminus, N-terminus, and/or within the native sequence. It is understood that such variants having added, substituted and/or additional amino acids retain one or more characterizing portions of the native PTK/adaptor complex, as described above.

A functional derivative of PTK/adaptor complexes comprising PTK and/or adaptor proteins with deleted, inserted and/or substituted amino acid residues may be prepared using standard techniques well-known to those of ordinary skill in the art. For example, the modified components of the functional derivatives may be produced using site-directed mutagenesis techniques (as exemplified by Adelman et al., 1983, DNA 2:183) wherein nucleotides in the DNA coding the sequence are modified such that a modified coding sequence is modified, and thereafter expressing this recombinant DNA in a prokaryotic or eukaryotic host cell, using techniques such as those described above. Alternatively, components of functional derivatives of PTK/adaptor complexes with amino acid deletions, insertions and/or substitutions may be conveniently prepared by direct chemical synthesis, using methods well-known in the art. The functional derivatives of the PTK/adaptor complexes typically exhibit the same qualitative biological activity as the native complexes.

5.5 PROGNOSTIC EVALUATION OF PTK/ADAPTOR-RELATED ONCOGENIC DISORDERS

The PTK/adaptor protein complexes of the invention involved in oncogenic disorders may be utilized in developing a prognostic evaluation of the condition of a patient suspected of exhibiting such an oncogenic disorder. For example, biological samples obtained from patients suspected of exhibiting an oncogenic disorder involving a PTK/adaptor protein complex may be assayed for the presence of such complexes. If such a PTK/adaptor protein complex is normally present, and the development of the oncogenic disorder is caused by an abnormal quantity of the complex, the assay should compare complex levels in the biological sample to the range expected in normal, non-oncogenic tissue of the same cell type.

Among the assays which may be undertaken may include, but are not limited to isolation of the PTK/adaptor protein complex of interest from the biological sample, or assaying for the presence of the complex by exposing the sample to an antibody specific for the complex, but non-reactive to any single, non-complexed component, and detecting whether antibody has specifically bound.

Alternatively, one or more of the components of the PTK/adaptor protein complex may be present in an abnormal level or in a modified form, relative to the level or form expected is normal, non-oncogenic tissue of the same cell type. For example, as demonstrated in the Working Examples presented in Sections 8 and 9, below, HER2 and/or GRB-7 are overexpressed in breast cancer cells, and the molecules form a tight HER2/GRB-7 complex. It is possible that overexpression of both GRB-7 and HER2 may indicate a particularly aggressive course of cancer. Thus, an assessment of the HER2 and GRB-7 levels of mRNA and protein in breast cancer tissue cells may provide valuable clues as to the course of action to be undertaken in treatment of such an oncogenic disorder. Assays of this type are well known to those of skill in the art, and may include, but are not limited to, Northern blot analysis, RNAse protection assays, and PCR for determining mRNA levels. Assays determining HER2 and GRB-7 protein levels are also well known to those of skill in the art, and may include, but are not limited to, Western blot analysis, immunoprecipitation, and ELISA analysis. Each of these techniques may also reveal potential differences in the form (e.g., the primary, secondary, or tertiary amino acid sequence, and/or post-translational modifications of the sequence) of the component(s).

Having now generally described the invention, the same will be more readily understood through reference to the following examples, which are provided by way of illustration, and are not intended to be limiting of the present invention.

6. EXAMPLE
GRB-7 LOCALIZES TO MOUSE CHROMOSOME 11 NEAR HER2/ERBB-2

In this example, it is demonstrated that the adaptor protein GRB-7 maps to a region of mouse chromosome 11 which also contains the receptor PTK/HER2/erbB-2. This region of the mouse chromosome 11 is syntenic to a region of human chromosome 17q that is often amplified in breast cancer (Buchberg et al., 1989, Genetics, 122:153–161; van de Vijver et al., 1987, Mol. Cell Biol., 7:2019–2023; Slamon et al., 1987, Science, 235:177–182). This region on 17q lies proximal to the locus containing the breast cancer susceptibility gene, BRCAl (Bowcock et al., 1993 Am. J. Hum. Genet. 52:718–722).

6.1 MATERIALS AND METHODS

Chromosome mapping. The interspecific backcross between (AEJ/Gn-a bpHabpH×*Mus spretus*) F1×AEJ/Gn-a bpH/abpH was previously described (Marini et al., 1993, Genomics, 15:200–202). Genomic DNA extractions, restriction endonuclease digestions, agarose gel electrophoresis, and Southern blot transfers, hybridizations and washes were described (Ma et al., 1993, Proc. Natl. Acad. Sci. USA, 90:6350–6354). DNA oligonucleotides used for detecting the SSLP marker was made using an Applied Biosystems Model 393 DNA synthesizer. SSLP markers were detected by amplifying genomic DNA from N2 animals using the specified DNA oligonucleotide pairs (Dietrich et al., 1992, Genetics, 131:423–447) and Taq DNA polymerase as described (Ma et al., 1993, Proc. Natl. Acad. Sci. USA, 90:6350–6354). The results of the interspecific backcrosses were analyzed by calculating the maximum likelihood estimates of linkage parameters as described by Green (1981, in the "Mouse in Biomedical Research", Academic Press, New York, pp. 91–104).

Southern blotting. Genomic DNA was prepared from tissue culture cells using standard techniques (Sambrook et al., 1989, Molecular Cloning. A Laboratory Manual, Cold Spring Harbor Laboratory Press, Cold Spring Harbor). Ten micrograms of DNA was digested with EcoR1 or Hind III and separated on 0.7% agarose gel. The DNA was transferred to Nytran (Schleicher and Schuell) using capillary action and crosslinked by ultraviolet light. The blot was blocked for 4 hours at 42° C. in hybridization buffer (40% Formamide, 20× Denhardt's, 1% SDS, 6× SSC and 100 µg/ml salmon sperm DNA) and then incubated with probe ($2 \times 10^6$ dpm/ml) overnight at 42° C. The probe consisted of a PCR product from mouse GRB-7 encompassing nucleotides 1437 to 1909. The probe was labelled with $^{32}$P-dCTP using a random priming kit (USB). The blots final wash was 0.5× SSC, 0.1% SDS, 42° C. To determine GRB-7 chromosomal localization, liver genomic DNA from inbred and recombinant inbred (RI) strains of mice was digested with TaqI and typed by Southern blotting as described previously (Sap et al., 1990, Proc. Natl. Acad. Sci. USA, 87:6112–6116). This analysis revealed two allelic forms of GRB-7, whose inheritance in RI strains of mice defined a single locus. Comparison of the strain distribution pattern for GRB-7 to those for 1124 other markers distributed over all of the mouse chromosomes allowed GRB-7 to be localized to chromosome 11 on the basis of its tight linkage to markers such as HoxB (1 recombinant among 31 informative RI strains scored), Gfap (5 recombinants among 52 strains), and Krt-1 (1 recombinant among 31 strains).

6.2 RESULTS

To refine the localization of GRB-7, its location on mouse chromosome 11 was determined in an interspecific backcross, that has been typed for over 30 genetic markers distributed throughout its length. Genomic DNAs from AEJ/Gn and Mus spretus parental control animals were digested with several restriction endonucleases and analyzed by Southern blot hybridization using probes that identified the following loci; Ngfr, Grb-7, Erbb-2, and Csfg. See Table 1, below:

TABLE 1

List of loci mapped in interspecific backcross animals.

| Locus | Probe Name | Restriction Enzyme | AEJ/Gn fragment sizes (kb) | M. spretus fragment sizes (kb)[a] |
|---|---|---|---|---|
| Ngfr | p5b | PstI | 4.0, 2.9 | 5.5, 2.4, 2.4, 1.5, 1.2 |
| Grb-7 | | TaqI | 2.6 | 1.9, 1.5, 1.2 |
| ErbB-2 | neuc(t)/sp6400 | PstI | 5.1 | 3.8 |
| Csfg | pBRG-4 | TaqI | 3.0 | 2.5 |
| Csfg | pBRG-4 | TaqI | 3.0 | 2.5 |
| D11Mit10[b] | | | 0.096 | 0.126 |

[a]Underlined restriction fragment size indicates the segregating allele(s) that was typed in the backcross.
[b]Locus typed by PCR amplification of microsatellite sequences.

At least one restriction fragment length polymorphism (RFLP) was identified for each of the probes tested and the sizes of the genomic restriction fragments detected by each probe are listed in Table 1, above. To determine the size polymorphism for D11Mit10, parental DNAs and F1 controls were polymerase chain reaction (PCR) amplified using the oligomers defining D11Mit10. As expected, a simple sequence length polymorphism (SSLP) was detected between AEJ/Gn and M. spretus (Table 1).

The segregation pattern of the M. spretus allele in 191 backcross animals was then determined for Ngfr, Grb-7, ErbB-2, and Csfg (by Southern blot hybridization) and for D11Mit10 by PCR amplification and agarose gel electrophoresis. The results are summarized in FIG. 2A. Mice were either homozygous for the AEJ/Gn allele or heterozygous for the M. spretus and AEJ/Gn alleles. The frequency of AEJ/Gn and M. spretus alleles for the loci mapped in the N2 progeny did not significantly differ from the expected 1:1 ratio. The results presented here are consistent with the previous genetic localization of Ngfr, ErbB-2, and Csfg, using a [(C57BL/6J×M. spretus)×C57BL/6J] interspecific backcross (Buchberg et al., 1989), Genetics, 122:153–161. Gene order was determined by minimizing the number of multiple recombinants between loci. The order of the loci and the ratio of the number of recombinants to the total number of N2 offspring examined for each locus are: Ngfr-5/191-(Grb-7, ErbB-2, Csfg)-6/191-D11Mit10. The genetic distances between the loci in centimorgans+/– standard error are: Ngfr-2.6+/–1.1-(Grb-7, ErbB-2, Csfg)-3.1+/–1.2-D11Mit10. No recombinants were detected between Grb-7, ErbB-2 and Csfg in 191 N2 progeny, indicating that these loci are tightly linked and must lie <1.6 cM apart (upper 95% confidence limit).

7. EXAMPLE
GRB-7 IS AMPLIFIED AND OVEREXPRESSED IN BREAST CANCER CELL LINES, AND IS OVEREXPRESSED IN BREAST CANCER TISSUE.

In this example, it is demonstrated that GRB-7 IS amplified and overexpressed in several different breast cancer cell lines. Further, it is shown that GRB-7 overexpression is also found in tissue samples from human breast cancer. This overexpression correlates with HER2 expression indicating that these two genes are often coamplified and coexpressed.

7.1 MATERIALS AND METHODS

Tissue Culture. Breast cancer cell lines were originally obtained from the ATCC and grown in DMEM, 4500 mg/dl glucose with penicillin/streptomycin and 10% Fetal Calf Serum. All NIH 3T3 cells were grown in the same media but using 10% calf serum. NIH 3T3 cells expressing the EGFR/HER2 chimera were obtained from Dr. A. Zilberstein and Dr. A. Ullrich. For experiments, cells were starved as described in the figure legends.

Immunoprecipitation and immunoblotting. Several rabbit polyclonal antibodies were generated against GRB-7. Three antibodies were generated against GST fusion proteins of GRB-7 consisting of amino acid 419–535 (#191), amino acid 297–535 (#193) and the full length protein (#222). An antipeptide antibody was generated against amino acid sequences 264–279 (#188). Antibodies were either used as whole serum or were affinity purified. For affinity purification, the fusion protein or peptide was immobilized on Affi-gel 10 (Biorad). Serum was concentrated by 50% ammonium sulfate precipitation and dissolved in 10 mM Tris, pH 7.5. The ammonium sulfate precipitated antibodies were then purified on the antigen column as described (Harlow and Lane, 1988, "Antibodies, a Laboratory Manual", Cold Spring Harbor Laboratory Press, Cold Spring Harbor) eluting the antibody with 100 mM Glycine, pH 2.5. Immunoprecipitation and immunoblotting in the cell lines were performed as previously described (Margolis et al., 1989, Cell, 57:1101–1107). Immunoblotting of the breast tumor samples with the GRB-7 antibody was performed using 100 mg of sodium dodecyl sulfate-solubilized protein extract as previously described (Tandon et al., 1989, J. Clin. Oncol., 1:1120–1128). SHC antibodies were purchased from Signal Transduction Labs (Lexington, Ky.). Rabbit polyclonal antibodies directed against the carboxyterminus of HER2 were generously provided by Dr. A. Zilberstein. Rabbit polyclonal antiphosphotyrosine antibodies were prepared using standard techniques (Kamps and Sefton, 1988, Oncogene, 5:1403–1408).

7.2 RESULTS

It was determined that GRB-7 is amplified and overexpressed with HER2 in breast cancer. The expression of GRB-7 was checked in several breast cancer cell lines by immunoblotting cell lysates for GRB-7 expression. A close correlation was found between HER2 and GRB-7 expression (FIG. 3A). To confirm that this overexpression was due to gene amplification, southern blotting with a GRB-7 probe was performed (FIG. 3B). GRB-7 is amplified in both SKBR-3 cells and BT-474, two cell lines in which HER2 is also amplified (Kury et al., 1990, Oncogene, 5:1403–1408). Neither GRB-7 nor HER2 is amplified in the other cell lines.

Immunoblotting with the GRB-7 antibody was performed on 72 breast cancer samples in which HER2 expression had previously been analyzed, also by an immunoblot procedure (Ciolla et al., 1992, JNCI, 84:1279–1282). A representative result of ten such tumors is displayed in FIG. 3C. Thirty four of the breast cancer specimens exhibited HER2 overexpression, and 24 of these were concomitantly positive for GRB-7 Expression. See Table 2, below.

TABLE 2

Correlation of GRB-7 expression with HER2 overexpression in human breast tumors[a]

|  | HER2[b] Negative | HER2 Positive |
|---|---|---|
| GRB-7 Negative | 30 | 10 |
| GRB-7 Positive | 8 | 24 |

[a]Significance p < 0.001
[b]HER2 overexpression was determined by immunoblotting as previously described (Ciocca et al., JNCI 84:1279, 1992)

In the 38 tumors negative HER2 for overexpression, only 8 were positive for GRB-7. These results were statistically significant by chi-square analysis (p<0.001), analysis and they confirm that GRB-7 is often expressed in human breast tumors in concert with HER2 overexpression.

Other genes on human chromosome 17q have also been found to be coamplified with HER2. Although c-erbA/Thyroid hormone receptor is coamplified with HER2, overexpression of this protein has not been detected (van de Vijver et al., 1987 Mol. Cell. Biol. 7:2019–2023; Tavassoli et al., 1989, British J. of Cancer 60:505–510). Topoisomerase IIa has been found to be coamplified with HER2 but in a relatively small percentage of the cases (Smith et al., 1993, Oncogene 8:933–938). The results presented herein indicate that GRB-7 is likely present in an amplicon which also contains HER2 and which represents a region on 17q.

8. EXAMPLE
GRB-7 BINDS TIGHTLY TO HER2 AND ALSO BINDS SHC.

In the Working Example presented herein, it is demonstrated that not only are the adaptor protein GRB-7 and the receptor PTK HER2 often coexpressed in breast cancer cells (as was shown, above, in the Working Example presented in Section 7) but also that GRB-7 binds to HER2 via its SH2 domain. This binding is significant as almost all of the tyrosine phosphorylated HER2 in the breast cancer cells examined coimmunoprecipitate with GRB-7 antibodies.

It is also demonstrated that the adaptor protein GRB-7 binds not only HER2 but also binds the tyrosine phosphorylated protein SHC. The binding of GRB-7 to SHC provides insight into the tyrosine phosphorylation sites to which the GRB-7 SH2 domain can bind.

8.1 MATERIALS AND METHODS

GRB-7 constructs. GST fusion proteins were generated by polymerase chain reaction of GRB-7 incorporating BamH1 restriction sites into the priming oligonucleotides. For the GST GRB-7 SH2 domain probe, the sequence encoding amino acids 419–535 was amplified, digested with Bam H1 and ligated into Bam H1 digested pGSTag vector (Ron and Dressler, 1992, Biotechniques, 13:866–869).

For mammalian expression of GRB-7, GRB-7 was cut from the λ Exlox plasmid with Xbal and Mse1 and blunt ended using Klenow fragment. This blunt end fragment as ligated into EcoRV digested PMJ30 vector (Margolis et al., 1990, Science, 248:607–610).

GST Blotting. The pGSTag constructs were labelled with γ32p-ATP as described using 0.2 U/μl protein kinase A (Ron and Dressler, 1992, Biotechniques, 13:866–869). Blots were incubated for 2 hours at room temperature in block buffer (20 mM Hepes, pH 7.5, 5 mM $MgCl_2$, 1 mM KCl, 5 mM DTT, 5% nonfat dry milk, 0.02% sodium azide) and probed for two hours at room temperature, in the same buffer, using 12.5 ng (3×10$^5$ dpm) per ml of probe. Blots were washed four times for 15 minutes with Tris Buffered Saline (10mM Tris pH 7.5, 150 mM NaCl) containing 0.1% Triton-100 before exposing.

All other methods are as presented, above, in Sections 6.1 and 7.1.

8.2 RESULTS

It was determined here that the GRB-7 protein is physically associated with the HER2 receptor. To perform these studies, GRB-7 was immunoprecipitated from starved SKBR-3 cells and then blotted with phosphotyrosine or HER2 antibodies. Antibodies to GRB-7 specifically immunoprecipitated a phosphotyrosine containing band at 190 kDa (FIG. 4A, left panel) which was identified as HER2 (FIG. 4A, middle panel). This coimmunoprecipitation was not seen with preimmune serum. No other bands were detected in the antiphosphotyrosine blot indicating that GRB-7, was not tyrosine phosphorylated (FIG. 4A, middle and right panels). This coimmunoprecipitation between GRB-7 and HER2 was demonstrated with three different GRB-7 antisera indicating it was not dependent on the antibody used. The coimmunoprecipitation of GRB-7 and HER2 was also seen in BT474 cells.

To determine what percentage of HER2 was bound to GRB-7 in these cells, GRB-7 was immunoprecipitated from a small number of cells such that the lysate could be depleted of GRB-7. Under these conditions, the lysates were almost completely cleared of tyrosine phosphorylated HER2 as well as GRB-7 (FIG. 4B). Preimmune serum which did not immunoprecipitate GRB-7 did not significantly affect the tyrosine phosphorylated HER2 in the lysates. It should be noted that GRB-7 immunoprecipitation did not measurably affect the total amount of HER2 in the cell lysate as only a small fraction of HER2 is tyrosine phosphorylated and able to bind GRB-7. These results indicate a strong association between tyrosine phosphorylated HER2 and GRB-7.

It was next determined whether GRB-7 might become phosphorylated after stimulation of growth factor receptors. Because the true ligand for HER2 is still unclear (Peles et al., 1993, EMBO J., 12:961–971; Plowman, et al., 1993, Nature 366:473–475), tyrosine phosphorylation was stimulated by activation of the EGF-Receptor in SKBR-3 cells (King et al., 1988, EMBO J., 7:1647–1651). After stimulation with EGF, several additional bands become tyrosine phosphorylated, yet tyrosine phosphorylation of GRB-7 was still undetectable (FIG. 5A). Phosphoamino acid analysis of GRB-7 before and after stimulation revealed the presence of phosphoserine and phosphothreonine but no phosphotyrosine.

It was found that GRB-7 antibodies immunoprecipitated a tyrosine phosphorylated protein of 54 kDa after EGF stimulation (FIG. 5A, right panel). It was suspected that this 54 kDa band might be tyrosine phosphorylated SHC (Pelicci et al., 1992 Cell, 70:93–104) as it has been found that another SH2 domain protein, GRB2, binds tightly to phosphorylated SHC (Rozakis Adcock et al., 1992 Nature, 360:689–692; Skolnik et al., 1993, EMBO J., 12:1929–1936). To confirm this, GRB-7 was immunoprecipitated from EGF stimulated SKBR-3 cells and immunoblotted with anti-SHC antibodies (FIG. 5B). It was possible to detect EGF stimulated association of SHC and GRB-7.

It was then determined whether GRB-7 binds directly to HER2 and SHC through the GRB-7 SH2 domain. The association of the GRB2 SH2 domain with SHC presumably occurs due to the tyrosine phosphorylation of SHC at residue 317 (Rozakis-Adcock et al., 1992, Nature, 360:689–692). The amino acid sequence around this tyrosine, YVN, is felt to represent a high affinity binding site for the SH2 domain of GRB2 when tyrosine phosphorylated. A similar motif is present in EGF-Receptor at tyrosine 1068 (YIN) and in HER2 at tyrosine 1139 (YVN). It was suspected that GRB-7 might also bind to both HER2 and SHC via binding of its SH2 domain to a similar motif. To study this problem, a GST fusion protein of the GRB-7 SH2 domain containing a protein kinase A phosphorylation site (Ron and Dressler, 1992, Biotechniques, 13:866–869). Phosphorylation by protein kinase A in the presence of $\gamma^{32}$P-ATP was then used to label the GST fusion protein. SKBR-3 lysates were separated by SDS-PAGE, transferred to nitrocellulose and probed with the labeled GRB-7 SH2 domain. During these incubations, one hundred fold molar excess of unlabeled GST, GST-GRB-7-SH2 or GST-GRB2 was added. With GST alone, the GRB-7 SH2 domain bound to two major bands at 190 kDA and 54 kDa, corresponding to HER2 and SHC (FIG. 6A, left panel). This demonstrates that GRB-7 can bind directly to these proteins in cells and does not require intermediate molecules. As expected, unlabeled GRB-7 competed the binding to both proteins (FIG. 6A, middle panel). It was found that GRB2 could prevent the GRB-7 SH2 domain from binding to SHC but did not affect HER2 binding (FIG. 6A, right panel).

When the same lysates were probed with $^{32}$p-labeled GRB2 at a similar concentration and specific activity as the GRB7-SH2 domain, GRB2 showed strong binding to SHC but no binding to HER2 (FIG. 6B). Binding of GRB2 to a protein at 160 kDA was detected. This protein is not HER2, but likely represents the association of the GRB2 SH3 domains to SOS (Li et al., 1993, Nature, 363:85–88; Egan et al., 1993, Nature, 363:45–51; Buday and Downward, 1993 Mol. Cell. Biol., 13:1903–1910; Rozakis-Adcock et al., 1993, Nature, 360:689–692). Unlabelled GRB-7 could not compete the binding of GRB2 to SHC in contrast to the fact that GRB2 could easily compete GRB-7 binding to SHC. Taken together, these results indicate that GRB-7 binds SHC probably at the same Y(V/I)N motif as GRB2. However, the affinity of GRB2 for SHC appears much greater than that of GRB-7. In contrast, GRB-7 binds tightly to HER2, but GRB2 does not compete this binding.

The binding of GRB-7 to SHC was of a lower affinity than GRB2 to SHC, but because cells overexpress GRB-7, the association of SHC with GRB-7 was detectable by coimmunoprecipitation. It seems likely that the GRB7 SH2 domain binds a Y(V/I)N (SEQ ID NO:15) motif but with a lower affinity than GRB2. GRB2 which competes the binding of GRB-7 to SHC does not affect the binding of GRB-7 to HER2 in the SKBR-3 cells. This suggests that GRB7 binds to a site other than Y(V/I)N on HER2, or binds to the Y(VI)N site on HER2, but with a much greater affinity than GRB2.

9. EXAMPLE

GRB-7 IS PHOSPHORYLATED BY THE EGFR/HER2 CHIMERA

It is demonstrated in the Working Example presented in this Section that GRB-7 is tyrosine phosphorylated in EGF stimulated cells expressing a chimeric EGFR/HER2 receptor. While the phosphorylation state of GRB-7 in vivo in breast tumors remains to be determined, there is a distinct possibility that the binding of GRB-7 to the receptor may be sufficient to initiate the GRB-7 signaling pathway.

9.1 MATERIALS AND METHODS

All methods presented herein are as described, above, in Sections 6.1, 7.1, and 8.1.

9.2 RESULTS

To determine if GRB-7 was tyrosine phosphorylated by activated HER2, GRB-7 was transfected into NIH 3T3 cells containing the chimeric EGF HER2 receptor (Lee et al., 1989, EMBO J., 8:167–173). These cells contain the HER2 intracellular domain fused to the EGF-Receptor extracellular domain such that EGF can stimulate the HER2 tyrosine kinase. After EGF stimulation of these cells, GRB-7 becomes tyrosine phosphorylated and associates with the chimeric receptor in a ligand dependent fashion (FIG. 7A). EGF also induces association between GRB-7 and an unidentified tyrosine phosphorylated protein of 70 kDa. The binding of the $^{32}$P-GRB-7 SH2 domain to lysates from NIH 3T3 cells expressing the EGFR/HER2 chimera was then examined (FIG. 7B). Binding to three bands was detected: the chimeric receptor at 190 kDa, the 54 kDa SHC band, and the unidentified band at 70 kDa. The binding of the GRB-7 SH2 domain to these proteins was enhanced in lysates from EGF stimulated cells. There was some binding of the probe to the receptor even in the absence of ligand because the receptor is autophosphorylated to some extent in the untreated cells. GRB2 was able to completely compete the binding of the GRB-7 SH2 domain to SHC but did not significantly affect the binding to the 70 kDa protein. GRB2 weakly competed with GRB-7 for binding to the chimeric receptor.

10. EXAMPLE
PRIMARY SEQUENCE OF GRB-7 REVEALS HOMOLOGY TO A PUTATIVE GENE IN C. ELEGANS AND THE PLECKSTRIN DOMAIN

It is demonstrated in the Working Example presented herein that the GRB-7 protein contains a sequence similar to the recently described pleckstrin domain. The proteins in which the pleckstrin domain is found are theorized to have a role in binding other regulatory proteins.

10.1 MATERIALS AND METHODS

DNA analysis. All DNA and protein database searches were performed using the University of Wisconsin Genetics Computer Group Sequence Analysis Software (GCG) package (Devereux et al., 1984, Nucleic Acid Res., 12:387–395). The GenEMBL database were searched using Fasta and Tfasta respectively (Pearson and Lipman, 1988, Proc. Natl. Acad. Sci. USA, 85:2444–2448). Protein alignments were performed with the GCG program, Bestfit. Conservative substitutions were defined as a score of ≧0.8 using the scoring table of Schwartz and Dayhoff (Schwartz and Dayhoff, 1979, in "Atlas of protein sequences and structure" Dayhoff, M. O., ed., pp. 353–358, National Biomedical Research Foundation, Washington, D.C.) as modified by Gribskov et al. (Gribskov, M., et al., 1984, Nucleic Acid Res., 12:539–549).

10.2 RESULTS

The data presented in the Working Examples, above, indicate that GRB-7 is a signaling partner for HER2, especially in breast cancer cells where both are overexpressed. However, it is not clear what signal might be sent by GRB-7 when it binds, and perhaps becomes phosphorylated by, HER2. A close similarity between GRB-7 and a putative gene identified by the C. elegans genome sequencing project (Sulston et al., 1992, Nature, 356:37–41) has now been identified. This putative C. elegans gene, F10E9.6, encodes a predicted protein of 650 amino acids with no SH2 domain. (FIG. 8A).

The region of similarity spans approximately 330 amino acids with an identity of 28% and similarity of 38% (FIG. 8B). Using the randomization utility of the alignment program Bestfit (Devereux et al., 1984, Nucleic Acid Res., 12:387–395) it was found that the optimal alignment score for GRB-7 to F10E9.6 lies more than 18 standard deviations from the mean of scores from ten scrambled alignments. This indicates a highly significant relationship between the two proteins, and indicates that the two genes are likely to function in a similar fashion.

This region of similarity between F10E9.6 and GRB-7 contains a pleckstrin domain. First described by Mayer and coworkers (Mayer et al., 1993, Cell, 73:629–630) as well as Haslam and coworkers (Haslam et al., 1993, Nature, 363:309–310), the pleckstrin domain is found in several different signaling molecules including pleckstrin (Tyers et al., 1988, Nature, 33:470–473), the serine kinase akt/rac (Jones et al., 991, Proc. Natl. Acad. Sci. USA, 88:4171–4175; Bellacosa et al., 1991, Science, 254:274–277), rasGAP (Vogel et al., 1988, Science 259:1611–1614; Trahey et al., 1988, Science 242:1697–1700), and the SH3 binding protein, 3BP-2 (Ren et al., 1993, Science, 259:1157–1161). In fact, the similarity initially detected between RasGAP and GRB-7 encompasses the pleckstrin domain (Margolis et al., 1992, Cell Growth Differ 3:73–80). It has been suggested that the pleckstrin motif may function as a protein binding domain (Mayer et al., 1993, Cell 73:629–630; Haslam et al., 1993, Nature 363:309–310; Musacchio et al., 1993, Trends Biochem. Sci. 18:343–348). An alignment of GRB-7, F10E9.6 and the derived consensus sequences for the pleckstrin domains is shown in FIG. 8C.

In addition to the pleckstrin domain, there is a second region of similarity which extends toward the amino terminus. Both GRB-7 and F10E9.6 have proline rich domains, which are potential sites for SH3 domains (Ren, R. et al., 1993, Science 259:1157–1161; Li, N., 1993, Nature 363:85–88).

While it is not known what signal is relayed by GRB-7, it is clearly a protein composed of evolutionarily conserved domains indicating that it likely performs a basic signaling function.

11. EXAMPLE
SCREENING ASSAY FOR INHIBITORS OF ADAPTOR PROTEIN TYROSINE KINASE INTERACTION

The Example presented herein describes a means for assessing the potential of a test substance to inhibit the interaction between an adaptor protein and an activated tyrosine kinase molecule. In this assay, an adaptor-GST fusion protein capable of binding to a phosphorylated tyrosine kinase protein is incubated with the phosphorylated tyrosine kinase protein, which has been immobilized on a solid surface, in the presence of a test substance. When the test substance is capable of inhibiting the interaction between the adaptor protein-GST fusion protein and the tyrosine kinase molecule, a decrease in the amount of adaptor-GST fusion protein bound to the immobilized tyrosine kinase molecule, relative to the amount of adaptor-GST fusion protein bound to the tyrosine kinase molecule in the absence of the test substance.

Adaptor-GST fusion protein: The adaptor-GST fusion proteins used herein are GRB-7-GST fusion proteins prepared by expression in *E. coli* transformed with GRB-7/pGEX constructs. Transformed cells are grown in Luria broth (LB) supplemented with ampicillin. After reaching an optical density (OD) at 600 nm of 0.3, the cells are induced for 6 hours with isopropyl β-D-thiogalactopyranoside (IPTG) in order to express the fusion protein.

After the 6 hour expression period, the cells are pelleted at 10,000×g for 10 minutes at 4° C., washed, and resuspended in phosphate buffered saline (PBS). Next, the cells are lysed by sonication (6 strokes, 5 seconds per stroke). Insoluble material is removed by centrifugation at 10,000×g for 10 minutes at 4° C., and the supernatant is passed over a Glutathion-Sepharose column. Bound GRB-7-GST fusion protein is eluted off the column with 5 mM reduced glutathion, then dialyzed against PBS.

Immobilized tyrosine kinase molecule: The tyrosine kinase molecule used herein is the HER2 receptor tyrosine kinase. HER2 is isolated from cells overexpressing HER2, such as the SKOV3 (ATCC HTB 77), SKBR3 (ATCC HTB 30), or BT474 (ATCC HTB 20), cell lines. The cells are lysed in HNTG buffer (20 mM Hepes/HCl, pH 7.4, 150 mM NaCl, 1.0% Triton X-100, 5% glycerol, 1 mM phenylmethylsulfonyl fluoride (PMSF), 1 mg/L aprotonin, 1 mg/L leupeptin, 10 mg/L benzamidine). HER2 protein is isolated from the cell lysates by immobilization onto microtiter plates, as described below. HER2 is generally fully phosphorylated after isolation.

The HER2 molecule is immobilized onto microtiter plates. Microtiter plates are prepared by first coating the wells of the plate, overnight at 4° C., with an anti-HER2 monoclonal antibody at a concentration of 0.5 μg (in PBS) per microtiter well, at a final volume of 150 μl per well. The anti-HER2 monoclonal antibodies are prepared by immunizing mice with HER2 extracellular domain peptides, and producing hybridomas utilizing standard methods, described, above, in Section 5.2.1.1. Monoclonal antibodies are purified by Protein A agarose chromatography. Antibodies are released from Protein A agarose by citric acid elution, immediately neutralized, and dialyzed into PBS.

After overnight coating, the coating solution is removed from the microtiter wells, and replaced with blocking buffer (5% dry milk in PBS) for 30 minutes at room temperature, after which the blocking buffer is removed and the wells are washed 4 times with TBST buffer (150 mM NaCl, 50 mM Tris-HCl, pH 7.2, 0.1% Triton X-100).

Cell lysate from HER2-expressing cells is added to each well, in 150 μl of PBS, incubated 30 minutes at room temperature, with shaking. Unbound HER2 is removed by washing wells 5 times with TBST buffer. Approximately 50 μg of HER2 protein is bound per well.

Assay procedure: 10–50 μg GRB-7-GST fusion proteins (i.e. a 5:1 to 1:1 ratio of HER2:GRB-7 proteins) are added to the HER2 coated microtiter wells in incubation buffer (0.1 M potassium phosphate buffer, pH 6.5) for 30 minutes, at room temperature, in the presence of a test substance dissolved in dimethyl sulfoxide (DMSO). Control wells are incubated with GRB-7-GST fusion proteins in the absence of test substance.

After incubation, wells are washed extensively with TBST. The amount of GRB-7-GST fusion protein bound to the immobilized HER2 is determined by incubating with 1 mM 1-chloro-2,4 dinitrobenzene (CDNB) and 1.54 mg/ml reduced glutathion in incubation buffer. The OD is then measured at 340 nm. This reaction is linear up to OD 1.0, and can be stopped with competitive GST inhibitors, as described in Mannervik and Danielson (Mannervik, B. and Danielson, U. H., 1988, CRC Critical Reviews in Biochemistry 23:238).

It is apparent that many modifications and variations of this invention as set forth here may be made without departing from the spirit and scope thereof. The specific embodiments described hereinabove are given by way of example only and the invention is limited only by the terms of the appended claims.

What is claimed is:

1. A method for identifying a compound that disrupts a receptor protein tyrosine kinase polypeptide/GRB-7 adaptor polypeptide complex comprising: exposing at least one compound to the coplex for a time sufficient to allow disruption of the complex, and detecting the disruption of the complex, so that if disruption of the complex has occurred, a compound that disrupts a receptor tyrosine kinase polypeptide/GRB-7 adaptor polypeptide complex is identified.

2. The method of claim 1 wherein the disruption of the receptor protein tyrosine kinase polypeptide/GRB-7 adaptor polypeptide complex is a separation of the complex components or a decrease in the activity of the complex.

3. A method for identifying a compound that disrupts or inhibits the formation of a receptor protein tyrosine kinase polypeptide/GRB-7 adaptor polypeptide complex comprising:

(a) contacting the compound with a cell that forms a receptor protein tyrosine kinase polypeptide/GRB-7 adaptor polypeptide complex for a time sufficient to allow intracellular binding of the compound to the receptor protein tyrosine kinase polypeptide or the GRB-7 adaptor polypeptide of the complex;

(b) detecting the level of the complex present in the cell of step (a);

(c) detect ing the level of the complex present in a cell of the type in step (a) that has not contacted the compound; and (d) comparing the level of the complex detected in step (b) to the level detected in step (c), so that if the level detected in step (c) is greater than the level detected in step (b), a compound that disrupts or inhibits the formation of a receptor protein tyrosine kinase polypeptide/GRB-7 adaptor polypeptide complex is identified.

4. The method of claim 3 wherein the level of receptor protein tyrosine kinase polypeptide/GRB-7 adaptor polypeptide complex is the amount of the complex present in the cell, or is the activity of the complex present in the cell.

5. A method for identifying a compound that disrupts a HER2 receptor protein tyrosine kinase polypeptide/GRB-7 adaptor polypeptide complex comprising: exposing at least one compound to the complex for a time sufficient to allow disruption of the complex, and detecting the disruption of the complex, so that if disruption of the complex has occurred, a compound that disrupts or inhibits the formation of a HER2 receptor tyrosine kinase polypeptide/GRB-7 adaptor polypeptide complex is identified.

6. The method of claim 5 wherein the disruption of the HER2 receptor protein tyrosine kinase polypeptide/GRB-7 adaptor polypeptide complex is a separation of the complex components or a decrease in the activity of the complex.

7. A method for identifying a compound tested for an ability to modulate an oncogenic disorder that disrupts or inhibits the formation of a HER2 receptor protein tyrosine kinase polypeptide/GRB-7 adaptor polypeptide complex comprising:

(a) contacting the compound with a cell that forms a HER2 receptor protein tyrosine kinase polypeptide/GRB-7 adaptor polypeptide complex for a time sufficient to allow intracellular binding of the compound to the HER2 receptor protein tyrosine kinase polypeptide or the GRB-7 adaptor polypeptide of the complex;

(b) detecting the level of the complex present in the cell of step (a);

(c) detecting the level of the complex present in a cell of the type in step (a) that has not contacted the compound; and (d) comparing the level of the complex detected in step (b) to the level detected in step (c), so that if the level detected in step (c) is greater than the level detected in step (b), a compound that disrupts or inhibits the formation of a HER2 receptor protein tyrosine kinase polypeptide/GRB-7 adaptor polypeptide complex is identified.

8. The method of claim 7 wherein the level of HER2 receptor protein tyrosine kinase polypeptide/GRB-7 adaptor polypeptide complex is the amount of the complex present in the cell, or is the activity of the complex present in the cell.

9. A method for identifying a compound that inhibits formation of a receptor protein tyrosine kinase polypeptide/GRB-7 adaptor polypeptide complex comprising:

(a) exposing a compound to a receptor tyrosine kinase polypeptide and a GRB-7 adaptor polypeptide for a time sufficient to allow formation of the receptor tyrosine kinase polypeptide/GRB-7 adaptor polypeptide complex;

(b) detecting the level of complex formed; and (c) comparing the level in (b) to the level of complex formed in the absence of the compound, so that if the level in (b) is lower than the level formed in the absence of the compound, a compound that inhibits formation of a receptor protein tyrosine kinase polypeptide/GRB-7 adaptor polypeptide complex is identified.

10. A method for identifying a compound that disrupts formation of a HER2 receptor protein tyrosine kinase polypeptide/GRB-7 adaptor polypeptide complex comprising:

(a) exposing a compound to a HER2 receptor tyrosine kinase polypeptide and a GRB-7 adaptor polypeptide for a time sufficient to allow formation of the HER2 receptor tyrosine kinase polypeptide/GRB-7 adaptor polypeptide complex;

(b) detecting the level of complex formed; and (c) comparing the level in (b) to the level of complex formed in the absence of the compound, so that if the level in (b) is lower than the level formed in the absence of the compound, a compound that disrupts formation of a HER2 receptor protein tyrosine kinase polypeptide/GRB-7 adaptor polypeptide complex is identified.

* * * * *

```
                       SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
           (A) LENGTH: 6 amino acids
           (B) TYPE: amino acid
           (C) STRANDEDNESS: single
           (D) TOPOLOGY: unknown (ii) MOLECULE TYPE: peptide (xi) SEQUENCE DESCRIPTION: SEQ ID NO:1:

Gly Xaa Gly Xaa Xaa Gly
1               5

(2) INFORMATION FOR SEQ ID NO:2:

(i) SEQUENCE CHARACTERISTICS:
           (A) LENGTH: 4 amino acids
           (B) TYPE: amino acid
           (C) STRANDEDNESS: single
           (D) TOPOLOGY: unknown
```

```
        (ii) MOLECULE TYPE: peptide (xi) SEQUENCE DESCRIPTION: SEQ ID NO:2:

Val Ala Val Lys
1

(2) INFORMATION FOR SEQ ID NO:3:

(i) SEQUENCE CHARACTERISTICS:
            (A) LENGTH: 5 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:3:

Gly Met Xaa Tyr Leu
1               5

(2) INFORMATION FOR SEQ ID NO:4:

(i) SEQUENCE CHARACTERISTICS:
            (A) LENGTH: 9 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:4:

Ile His Arg Asp Leu Ala Ala Arg Asn
1               5

(2) INFORMATION FOR SEQ ID NO:5:

(i) SEQUENCE CHARACTERISTICS:
            (A) LENGTH: 6 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:5:

Lys Trp Met Ala Pro Glu
1               5

(2) INFORMATION FOR SEQ ID NO:6:

(i) SEQUENCE CHARACTERISTICS:
            (A) LENGTH: 6 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:6:

Lys Trp Thr Ala Pro Glu
1               5

(2) INFORMATION FOR SEQ ID NO:7:

(i) SEQUENCE CHARACTERISTICS:
            (A) LENGTH: 6 amino acids
            (B) TYPE: amino acid
            (C) STRANDEDNESS: single
            (D) TOPOLOGY: unknown
```

(ii) MOLECULE TYPE: peptide (xi) SEQUENCE DESCRIPTION: SEQ ID NO:7:

Phe Trp Tyr Ala Pro Glu
1               5

(2) INFORMATION FOR SEQ ID NO:8:

(i) SEQUENCE CHARACTERISTICS:
            (A) LENGTH: 7 amino acids
            (B) TYPE: amino acid
            (C) STRANDEDNESS: single
            (D) TOPOLOGY: unknown (ii) MOLECULE TYPE: peptide (xi) SEQUENCE DESCRIPTION: SEQ ID NO:8:

Ser Asp Val Trp Ser Phe Gly
1               5

(2) INFORMATION FOR SEQ ID NO:9:

(i) SEQUENCE CHARACTERISTICS:
            (A) LENGTH: 334 amino acids
            (B) TYPE: amino acid
            (C) STRANDEDNESS: single
            (D) TOPOLOGY: unknown (ii) MOLECULE TYPE: protein (xi) SEQUENCE DESCRIPTION: SEQ ID NO:9:

Arg Asp Ser Ser Arg Leu Cys Val Val Lys Val Tyr Ser Glu Asp Gly
1               5                   10                  15

Ala Cys Arg Ser Val Glu Val Ala Ala Gly Ala Thr Ala Arg His Val
                20                  25                  30

Cys Glu Met Leu Val Gln Arg Ala His Ala Leu Ser Asp Glu Ser Trp
            35                  40                  45

Gly Leu Val Glu Ser His Pro Tyr Leu Ala Leu Glu Arg Gly Leu Glu
        50                  55                  60

Asp His Glu Phe Val Val Glu Val Gln Glu Ala Trp Pro Val Gly Gly
65                  70                  75                  80

Asp Ser Arg Phe Ile Phe Arg Lys Asn Phe Ala Lys Tyr Glu Leu Phe
                85                  90                  95

Lys Ser Pro Pro His Thr Leu Pro Glu Lys Met Val Ser Ser Cys
            100                 105                 110

Leu Asp Ala Gln Thr Gly Ile Ser His Glu Asp Leu Ile Gln Asn Phe
        115                 120                 125

Leu Asn Ala Gly Ser Phe Pro Glu Ile Gln Gly Phe Leu Gln Leu Arg
    130                 135                 140

Gly Ser Gly Arg Gly Ser Gly Arg Lys Leu Trp Lys Arg Phe Phe Cys
145                 150                 155                 160

Phe Leu Arg Arg Ser Gly Leu Tyr Tyr Ser Thr Lys Gly Thr Ser Lys
                165                 170                 175

Asp Pro Arg His Leu Gln Tyr Val Ala Asp Val Asn Glu Ser Asn Val
            180                 185                 190

Tyr Val Val Thr Gln Gly Arg Lys Leu Tyr Gly Met Pro Thr Asp Phe
        195                 200                 205

Gly Phe Cys Val Lys Pro Asn Leu Arg Asn Gly His Lys Gly Leu
    210                 215                 220

```
His Ile Phe Cys Ser Glu Asp Glu Gln Ser Arg Thr Cys Trp Leu Ala
225                 230                 235                 240

Ala Phe Arg Leu Phe Lys Tyr Gly Val Gln Leu Tyr Lys Asn Tyr Gln
                245                 250                 255

Gln Ala Gln Ser Arg His Leu Arg Leu Ser Tyr Leu Gly Ser Pro Pro
            260                 265                 270

Leu Arg Ser Val Ser Asp Asn Thr Leu Val Ala Met Asp Phe Ser Gly
        275                 280                 285

His Ala Gly Arg Val Ile Asp Asn Pro Arg Glu Ala Leu Ser Ala Ala
    290                 295                 300

Met Glu Glu Ala Gln Ala Trp Arg Lys Lys Thr Asn His Arg Leu Ser
305                 310                 315                 320

Leu Pro Thr Thr Cys Ser Gly Ser Ser Leu Ser Ala Ala Ile
                325                 330
```

(2) INFORMATION FOR SEQ ID NO:10:

(i) SEQUENCE CHARACTERISTICS:
        (A) LENGTH: 348 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:10:

```
Lys Glu Ala Lys Val Thr Lys Ile Phe Val Lys Phe Val Glu Asp
1               5                   10                  15

Gly Glu Ala Leu Gln Leu Leu Ile Asp Glu Arg Trp Thr Val Ala Asp
                20                  25                  30

Thr Leu Lys Gln Leu Ala Glu Lys Asn His Ile Ala Leu Met Glu Asp
            35                  40                  45

His Cys Ile Val Glu Glu Tyr Pro Glu Leu Tyr Ile Lys Arg Val Tyr
    50                  55                  60

Glu Asp His Glu Lys Val Val Glu Asn Ile Gln Met Trp Val Gln Asp
65                  70                  75                  80

Ser Pro Asn Lys Leu Tyr Phe Met Arg Arg Pro Asp Lys Tyr Ala Phe
                85                  90                  95

Ile Ser Arg Pro Glu Leu Tyr Leu Leu Thr Pro Lys Thr Ser Asp His
            100                 105                 110

Met Glu Ile Pro Ser Gly Asp Gln Trp Thr Ile Asp Val Lys Gln Lys
    115                 120                 125

Phe Val Ser Glu Tyr Phe His Arg Glu Pro Val Val Pro Pro Glu Met
130                 135                 140

Glu Gly Phe Leu Tyr Leu Lys Ser Asp Gly Arg Lys Ser Trp Lys Lys
145                 150                 155                 160

His Tyr Phe Val Leu Arg Pro Ser Gly Leu Tyr Tyr Ala Pro Lys Ser
                165                 170                 175

Lys Lys Pro Thr Thr Lys Asp Leu Thr Cys Leu Met Asn Leu His Ser
            180                 185                 190

Asn Gln Val Tyr Thr Gly Ile Gly Trp Glu Lys Lys Tyr Lys Ser Pro
    195                 200                 205

Thr Pro Trp Cys Ile Ser Ile Lys Leu Thr Ala Leu Gln Met Lys Arg
210                 215                 220

Ser Gln Phe Ile Lys Tyr Ile Cys Ala Glu Asp Glu Met Thr Phe Lys
225                 230                 235                 240
```

-continued

```
Lys Trp Leu Val Ala Leu Arg Ile Ala Lys Asn Gly Ala Glu Leu Leu
                245                 250                 255

Glu Asn Tyr Glu Arg Ala Cys Gln Ile Arg Arg Glu Thr Leu Gly Pro
            260                 265                 270

Ala Ser Ser Met Ser Ala Ala Ser Ser Ser Thr Ala Ile Ser Glu Val
                275                 280                 285

Pro His Ser Leu Ser His His Gln Arg Thr Pro Ser Val Ala Ser Ser
            290                 295                 300

Ile Gln Leu Ser Ser His Met Met Asn Asn Pro Thr His Pro Leu Ser
305                 310                 315                 320

Val Asn Val Arg Asn Gln Ser Pro Ala Ser Phe Ser Val Asn Ser Cys
                325                 330                 335

Gln Gln Ser His Pro Ser Arg Thr Ser Ala Lys Leu
            340                 345
```

(2) INFORMATION FOR SEQ ID NO:11:

(i) SEQUENCE CHARACTERISTICS:
        (A) LENGTH: 111 amino acids
        (B) TYPE: amino acid
        (C) STRANDEDNESS: single
        (D) TOPOLOGY: unknown (ii) MOLECULE TYPE: protein (ix) FEATURE:
        (A) NAME/KEY: Modified-site
        (B) LOCATION: 1, 25-27, 32, 46, 47, 49, 52, 54, 72
            75, 77, 93, 95, 105, 107, 108 and 111
        (D) OTHER INFORMATION: /label= Xaa
           /note= "Xaa at these positions = Hydrophobic
           residues"

(ix) FEATURE:
        (A) NAME/KEY: Modified-site
        (B) LOCATION: 2, 21, 23 and 101
        (D) OTHER INFORMATION: /label= Xaa
           /note= "Xaa at these positions = Basic residues"

(ix) FEATURE:
        (A) NAME/KEY: Modified-site
        (B) LOCATION: 3, 7, 9, 11-19, 22, 28-31, 36-42, 44, 48
            50, 51, 53, 55-70, 74, 76, 78-90, 92, 94
            96-98, 106 109 and 110
        (D) OTHER INFORMATION: /label= Xaa
           /note= "Xaa at these positions = Non-consensus
           residues"

(ix) FEATURE:
        (A) NAME/KEY: Modified-site
        (B) LOCATION: 24, 33-35 and 91
        (D) OTHER INFORMATION: /label= Xaa
           /note= "Xaa at these positions = Aromatic
           residues"

(ix) FEATURE:
        (A) NAME/KEY: Modified-site
        (B) LOCATION: 99, 100, 102 and 103
        (D) OTHER INFORMATION: /label= Xaa
           /note= "Xaa at these positions = Acidic residues"

(xi) SEQUENCE DESCRIPTION: SEQ ID NO:11:

```
Xaa Xaa Xaa Gly Phe Leu Xaa Lys Xaa Gly Xaa Xaa Xaa Xaa Xaa Xaa
1               5                   10                  15

Xaa Xaa Xaa Trp Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Pro Xaa Gly Xaa Xaa Xaa
                35                  40                  45
```

```
Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Asn Xaa Phe Xaa Xaa Xaa Xaa Xaa Xaa
65                  70              75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Trp Xaa Xaa Xaa Xaa Xaa Xaa Xaa
            100                 105                 110
```

(2) INFORMATION FOR SEQ ID NO:12:

(i) SEQUENCE CHARACTERISTICS:
        (A) LENGTH: 111 amino acids
        (B) TYPE: amino acid
        (C) STRANDEDNESS: single
        (D) TOPOLOGY: unknown (ii) MOLECULE TYPE: protein (ix) FEATURE:
        (A) NAME/KEY: Modified-site
        (B) LOCATION: 1
        (D) OTHER INFORMATION: /label= Xaa
            /note= "Xaa = Isoleucine or Valine"

(ix) FEATURE:
        (A) NAME/KEY: Modified-site
        (B) LOCATION: 2, 69 and 102
        (D) OTHER INFORMATION: /label= Xaa
            /note= "Xaa at these positions = Arginine or
            Lysine"

(ix) FEATURE:
        (A) NAME/KEY: Modified-site
        (B) LOCATION: 5
        (D) OTHER INFORMATION: /label= Xaa
            /note= "Xaa = Tyrosine or Tryptophan"

(ix) FEATURE:
        (A) NAME/KEY: Modified-site
        (B) LOCATION: 7, 11-17, 22, 28, 29, 31, 33, 35, 38-42
            46, 47, 50-52, 58-68, 70, 72, 74, 76-78
            80-92, 96, 98, 109, 110
        (D) OTHER INFORMATION: /label= Xaa
            /note= "Xaa at these positions = Non-consensus
            residues"

(ix) FEATURE:
        (A) NAME/KEY: Modified-site
        (B) LOCATION: 8, 9, 18 and 21
        (D) OTHER INFORMATION: /label= Xaa
            /note= "Xaa at these positions = Lysine or
            Arginine"

(ix) FEATURE:
        (A) NAME/KEY: Modified-site
        (B) LOCATION: 19
        (D) OTHER INFORMATION: /label= Xaa
            /note= "Xaa = Threonine or Serine"

(ix) FEATURE:
        (A) NAME/KEY: Modified-site
        (B) LOCATION: 24
        (D) OTHER INFORMATION: /label= Xaa
            /note= "Xaa = Tryptophan or Tyrosine"

(ix) FEATURE:
        (A) NAME/KEY: Modified-site
        (B) LOCATION: 26 and 57
        (D) OTHER INFORMATION: /label= Xaa
            /note= "Xaa at these positions = Valine or
            Isoleucine"

(ix) FEATURE:
        (A) NAME/KEY: Modified-site

```
      (B) LOCATION: 30
      (D) OTHER INFORMATION: /label= Xaa
          /note= "Xaa = Aspartic Acid or Glycine"

(ix) FEATURE:
      (A) NAME/KEY: Modified-site
      (B) LOCATION: 34
      (D) OTHER INFORMATION: /label= Xaa
          /note= "Xaa = Leucine or Tyrosine"

(ix) FEATURE:
      (A) NAME/KEY: Modified-site
      (B) LOCATION: 36
      (D) OTHER INFORMATION: /label= Xaa
          /note= "Xaa = Tyrosine or Phenylalanine"

(ix) FEATURE:
      (A) NAME/KEY: Modified-site
      (B) LOCATION: 37
      (D) OTHER INFORMATION: /label= Xaa
          /note= "Xaa = Lysine or Glutamic Acid"

(ix) FEATURE:
      (A) NAME/KEY: Modified-site
      (B) LOCATION: 55
      (D) OTHER INFORMATION: /label= Xaa
          /note= "Xaa = Cysteine or Valine"

(ix) FEATURE:
      (A) NAME/KEY: Modified-site
      (B) LOCATION: 56
      (D) OTHER INFORMATION: /label= Xaa
          /note= "Xaa = Glutamine or Glutamic Acid"

(ix) FEATURE:
      (A) NAME/KEY: Modified-site
      (B) LOCATION: 71
      (D) OTHER INFORMATION: /label= Xaa
          /note= "Xaa = Asparagine or Histidine"

(ix) FEATURE:
      (A) NAME/KEY: Modified-site
      (B) LOCATION: 75 and 108
      (D) OTHER INFORMATION: /label= Xaa
          /note= "Xaa at these positions = Isoleucine
          or Leucine"

(ix) FEATURE:
      (A) NAME/KEY: Modified-site
      (B) LOCATION: 93
      (D) OTHER INFORMATION: /label= Xaa
          /note= "Xaa = Phenylalanine or Leucine"

(ix) FEATURE:
      (A) NAME/KEY: Modified-site
      (B) LOCATION: 94
      (D) OTHER INFORMATION: /label= Xaa
          /note= "Xaa = Glutamine or Alanine"

(ix) FEATURE:
      (A) NAME/KEY: Modified-site
      (B) LOCATION: 97
      (D) OTHER INFORMATION: /label= Xaa
          /note= "Xaa = Serine or Threonine"

(ix) FEATURE:
      (A) NAME/KEY: Modified-site
      (B) LOCATION: 102 and 103
      (D) OTHER INFORMATION: /label= Xaa
          /note= "Xaa at these positions = Glutamic Acid
          or Aspartic Acid"

(ix) FEATURE:
      (A) NAME/KEY: Modified-site
      (B) LOCATION: 105
      (D) OTHER INFORMATION: /label= Xaa
          /note= "Xaa = Valine or Methionine"

(ix) FEATURE:
```

-continued

```
            (A) NAME/KEY: Modified-site
            (B) LOCATION: 111
            (D) OTHER INFORMATION: /label= Xaa
                 /note= "Xaa = Alanine or Valine"

(xi) SEQUENCE DESCRIPTION: SEQ ID NO:12:

Ile Arg Glu Gly Tyr Leu Xaa Lys Lys Gly Xaa Xaa Xaa Xaa Xaa
1               5                   10                  15

Xaa Lys Thr Trp Lys Xaa Arg Trp Phe Val Leu Xaa Xaa Asp Xaa Leu
            20                  25                  30

Xaa Leu Xaa Tyr Lys Xaa Xaa Xaa Xaa Xaa Pro Lys Gly Xaa Xaa Pro
            35                  40                  45

Leu Xaa Xaa Xaa Ser Val Cys Gln Val Xaa Xaa Xaa Xaa Xaa Xaa
    50                  55                  60

Xaa Xaa Xaa Xaa Arg Xaa Asn Xaa Phe Xaa Ile Xaa Xaa Xaa Asp Xaa
65              70                  75                  80

Xaa Xaa Xaa Xaa Xaa Xaa Xaa Xaa Xaa Xaa Xaa Phe Gln Ala Xaa
            85                  90                  95

Ser Xaa Glu Glu Arg Glu Glu Trp Val Lys Ala Ile Xaa Xaa Ala
            100                 105                 110

(2) INFORMATION FOR SEQ ID NO:13:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:13:

Asp Leu Arg Ala Ala Asn
1               5

(2) INFORMATION FOR SEQ ID NO:14:

(i) SEQUENCE CHARACTERISTICS:
        (A) LENGTH: 8 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Modified-site
        (B) LOCATION: 2
        (D) OTHER INFORMATION: /label= Xaa
             /note= "Xaa = Isoleucine or Valine"

(ix) FEATURE:
        (A) NAME/KEY: Modified-site
        (B) LOCATION: 3
        (D) OTHER INFORMATION: /label= Xaa
             /note= "Xaa = Lysine or Arginine"

(ix) FEATURE:
        (A) NAME/KEY: Modified-site
        (B) LOCATION: 5
        (D) OTHER INFORMATION: /label= Xaa
             /note= "Xaa = Threonine or Methionine"

(xi) SEQUENCE DESCRIPTION: SEQ ID NO:14:

Pro Xaa Xaa Trp Xaa Ala Pro Glu
1               5
```

(2) INFORMATION FOR SEQ ID NO:15:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Modified-site
        (B) LOCATION: 5
        (D) OTHER INFORMATION: /label= Xaa
            /note= "Xaa = Valine or Isoleucine"

(ix) FEATURE:
        (A) NAME/KEY: Modified-site
        (B) LOCATION: 7
        (D) OTHER INFORMATION: /label= Xaa
            /note= "Xaa = Valine or Isoleucine"

(xi) SEQUENCE DESCRIPTION: SEQ ID NO:15:

Xaa Pro Xaa Tyr Xaa Asn Xaa
1               5

(2) INFORMATION FOR SEQ ID NO:16:

(i) SEQUENCE CHARACTERISTICS:
        (A) LENGTH: 10 amino acids
        (B) TYPE: amino acid
        (C) STRANDEDNESS: single
        (D) TOPOLOGY: unknown (ii) MOLECULE TYPE: peptide (ix) FEATURE:
        (A) NAME/KEY: Modified-site
        (B) LOCATION: 8
        (D) OTHER INFORMATION: /label= Xaa
            /note= "Xaa = Hydrophobic Residue"

(xi) SEQUENCE DESCRIPTION: SEQ ID NO:16:

Xaa Pro Xaa Xaa Pro Pro Pro Xaa Xaa Pro
1               5                   10

(2) INFORMATION FOR SEQ ID NO:17:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:17:

Pro Pro Val Pro Pro Arg Arg
1               5

(2) INFORMATION FOR SEQ ID NO:18:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:18:

Asp Leu Arg Ala Ala Asn

-continued (2) INFORMATION FOR SEQ ID NO:19:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:19:

Asp Leu Ala Ala Arg Asn
1               5

(2) INFORMATION FOR SEQ ID NO:20:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:20:

Phe Leu Ile Arg Glu Ser
1               5

(2) INFORMATION FOR SEQ ID NO:21:

(i) SEQUENCE CHARACTERISTICS:
        (A) LENGTH: 6 amino acids
        (B) TYPE: amino acid
        (C) STRANDEDNESS: single
        (D) TOPOLOGY: unknown (ii) MOLECULE TYPE: peptide (xi) SEQUENCE DESCRIPTION: SEQ ID NO:21:

Phe Leu Val Arg Glu Ser
1               5